(12) United States Patent
Hirt et al.

(10) Patent No.: US 12,119,143 B2
(45) Date of Patent: Oct. 15, 2024

(54) ELONGATED ELASTIC SEAM TAPE WITH ELECTRICAL CONDUCTOR

(71) Applicant: Nanoleq AG, Rümlang (CH)

(72) Inventors: Luca Hirt, Olten (CH); Flurin Stauffer, Zürich (CH); Vincent Martinez, Zürich (CH); Serge Alain Weydert, Zürich (CH)

(73) Assignee: Nanoleq AG, Rümlang (CH)

( * ) Notice: Subject to any disclaimer, the term of this patent is extended or adjusted under 35 U.S.C. 154(b) by 0 days.

(21) Appl. No.: 17/775,844

(22) PCT Filed: Nov. 10, 2020

(86) PCT No.: PCT/EP2020/081578
§ 371 (c)(1),
(2) Date: May 10, 2022

(87) PCT Pub. No.: WO2021/094284
PCT Pub. Date: May 20, 2021

(65) Prior Publication Data
US 2022/0392664 A1 Dec. 8, 2022

(30) Foreign Application Priority Data
Nov. 12, 2019 (EP) .................... 19208544

(51) Int. Cl.
*H01B 7/08* (2006.01)
*C09J 7/10* (2018.01)
*H01B 7/02* (2006.01)
*H01B 7/04* (2006.01)
*H01B 13/10* (2006.01)

(52) U.S. Cl.
CPC .................. *H01B 7/04* (2013.01); *C09J 7/10* (2018.01); *H01B 7/0225* (2013.01); *H01B 7/0258* (2013.01); *H01B 13/10* (2013.01); *C09J 2203/358* (2020.08); *C09J 2400/266* (2013.01)

(58) Field of Classification Search
CPC ...................................................... H01B 7/08
See application file for complete search history.

(56) References Cited

U.S. PATENT DOCUMENTS 4,425,475 A * 1/1984 Ward ....................... H01B 7/04
174/131 A
6,000,951 A * 12/1999 Hansen ................. H01R 12/79
439/496

(Continued)

FOREIGN PATENT DOCUMENTS

CN 108520794 A 9/2018
EP 3385348 10/2018

(Continued)

OTHER PUBLICATIONS

International Search Report and Written Opinion for PCT Application No. PCT/EP2020/081578 mailed Feb. 5, 2021.

(Continued)

*Primary Examiner* — Chau N Nguyen
(74) *Attorney, Agent, or Firm* — Branch Partners PLLC; Bruce E. Black

(57) ABSTRACT

The present invention relates to an elongated elastic seam tape comprising an elongated elastic conductor as well as to a method of manufacturing such an elongated elastic seam tape.

29 Claims, 22 Drawing Sheets

(56) References Cited

U.S. PATENT DOCUMENTS

| | | | |
|---|---|---|---|
| 6,020,559 A * | 2/2000 | Maeda | H05K 3/363 |
| | | | 174/117 FF |
| 6,096,978 A | 8/2000 | Pohjola | |
| 6,341,504 B1 * | 1/2002 | Istook | D04B 21/18 |
| | | | 66/172 E |
| 6,497,934 B1 | 12/2002 | Mahn, Jr. et al. | |
| 8,741,412 B2 | 6/2014 | Wangbunyen et al. | |
| 8,969,724 B2 * | 3/2015 | Tatsumi | H01B 11/02 |
| | | | 385/100 |
| 2013/0105215 A1 * | 5/2013 | Morris | H05K 9/0098 |
| | | | 174/394 |
| 2014/0272509 A1 * | 9/2014 | Thomas | H01M 50/367 |
| | | | 429/100 |
| 2017/0251732 A1 | 9/2017 | Furey | |
| 2018/0030224 A1 | 2/2018 | Humiston et al. | |
| 2018/0268958 A1 * | 9/2018 | Aoyama | H01B 7/02 |
| 2018/0315527 A1 * | 11/2018 | Lee | H01F 38/14 |
| 2018/0317849 A1 * | 11/2018 | Schibli | A61L 29/14 |

FOREIGN PATENT DOCUMENTS

| | | |
|---|---|---|
| JP | 2017174685 A | 9/2017 |
| WO | 96/35475 | 11/1996 |

OTHER PUBLICATIONS

European Search Report for EP Patent Application No. 19208544.7 mailed May 18, 2020.

* cited by examiner

ELONGATED ELASTIC SEAM TAPE WITH ELECTRICAL CONDUCTOR

CROSS-REFERENCE TO RELATED APPLICATIONS

This present application is a U.S. national stage application of PCT Application No. PCT/EP2020/081578, filed Nov. 10, 2020, which claims priority to European Patent Application No. 19208544.7 filed Nov. 12, 2019, both of which are hereby incorporated by reference in their entirety.

FIELD

The present invention relates to an elongated elastic seam tape comprising an elongated elastic conductor as well as to a method of manufacturing such an elongated elastic seam tape.

BACKGROUND

So-called electronic textiles, e-textiles or smart textiles are becoming more and more common to enhance the function and performance of textiles. While it is generally possible to manufacture textiles having these electronic capabilities already embedded therein, it is advantageous in many cases to simply "upgrade" a regular piece of textile to an e-textile by applying, for example, the required circuitry onto the textile. For this purpose, seam tapes including fiber-based circuitry and stretchable conductive films for textiles have been developed (see, e.g., US 2017/0251732 A1 and EP 3 385 348 A1).

However, these known seam tapes or stretchable conductive films are disadvantageous in that they are complicated and expensive to manufacture, difficult to electrically connect and complicated to electrically insulate. Furthermore, these tapes/films can change the mechanical properties of the original textile as well as negatively impact the wear comfort of the garment. These aspects limit their versatility and use. Because such seam tapes are often integrated in stretchable textiles, one important aspect is that the seam tape needs to be stretchable, preferably along all directions. Another important aspect is the possibility to connect conductors which are embedded in seam tapes to electronics. It is often difficult to electrically connect known conductive seam tapes in a robust way. The connection between conductors and additional electronics should, in addition, preferably be sealed from external influences, e.g. to avoid corrosion of the conductor due to contact with fluids during washing or sweating.

It is thus an object of the present invention to provide an improved elastic seam tape with a conductor as well as a method for manufacturing such an elastic seam tape which address the above-mentioned needs.

This object is achieved by an elongated elastic seam tape according to claim 1 and by a method of manufacturing an elongated elastic seam tape according to claim 17.

Accordingly, the present invention relates to an elongated elastic seam tape comprising an elongated elastic first layer, an elongated elastic second layer, partially bonded to the first layer, and an elongated elastic conductor. Each longitudinal edge of the second layer is, at least partially, bonded to a corresponding longitudinal edge of the first layer so as to form a lumen extending along the entire seam tape between the first and second layers. The conductor is movably positioned within said lumen.

In the context of the present invention, the term "seam tape" refers to a band-like or ribbon-like structure. Seam tapes may, e.g., be used for bonding textile layers together and/or for creating waterproof or water-resistant seams in garments. Seam tapes have a substantially flat or flat structure. In this way, they may be applied to textile layers. Moreover, seam tapes may inter alia comprise an adhesion layer, e.g., for bonding to a textile layer or garment, and a textile or polymer top layer. Seam tapes are, e.g., described in US 2018/0030224, U.S. Pat. No. 8,741,412 or U.S. Pat. No. 6,497,934.

In the context of the present invention, the term "elongated" refers to the dimensions of the elastic seam tape rather than to its state (stretched versus unstretched) and is supposed to cover any seam tape whose length is greater (preferably by at least a factor of 2) than its width.

In the context of the present invention, the term "elastic" refers to a material property of the seam tape and its constituents and requires that the seam tape (and each of its constituents) can be elastically stretched, at least along the length direction, by manually achievable forces and relaxes back into its unstretched state if the forces are no longer applied. Preferably, the seam tape and its constituents can be elastically stretched along the length direction and the width direction by manually achievable forces and relaxes back into its unstretched state if the forces are no longer applied. Preferably, the materials of the first and second layer as well as of the conductor have a Young's modulus between 10 kPa and 1 GPa, more preferably between 100 kPa and 100 MPa.

The lumen of the seam tape provides several advantages. First of all, a conductor can be withdrawn from the lumen and the conductor can move within the lumen, for example, when the seam tape is stretched along its longitudinal extension. Moreover, the lumen allows for an easy access to both ends of the conductor for attaching, for example, a connector as will be discussed further below. In addition, due to the movability of the conductor within the lumen, a preferred embodiment comprising a pre-stretched conductor within the lumen can be provided as also discussed further below.

The lumen extends along the entire length of the seam tape between the first and second layers and may, in a direction perpendicular to the plane defined by the extension of the first and second layers, extend into either or both of the first and second layers. For example, at the interface between the first and second layers, the surface of the first layer adjacent to the second layer may be essentially flat or planar and the second layer may comprise a groove or recession which defines the lumen. Alternatively, both layers may be deformed or recessed at their common interface so as to form a lumen which extends into both the first and second layers.

Preferably, the elongated elastic conductor is a soft conductor based on, e.g., a conductive composite material. Such a material is composed of at least one elastic matrix material and at least one conductive filler material. For example, the conductor material may be a silicone elastomer filled with dendritic silver microparticles. Above a certain particle content, the particles touch each other, thereby forming a conductive path in the conductive composite material. The conductor may have a diameter between 0.1 mm and 3 mm, preferably between 0.3 mm and 2 mm. The conductor need, however, not be round but could, for example, also have a flat profile with a thickness between 0.05 mm and 0.5 mm and a width between 0.5 mm and 3 mm. The particles preferably have an average size between 1 and 50 µm, more preferably between 10 and 30 µm. The particle content of the composite material is preferably between 20 and 35 vol. %. The resistance of the conductor is preferably between 1 Ω/m and 100 Ω/m at rest.

The conductor matrix may comprise one or a combination of the following materials: polyurethane, silicone rubber, polydimethylsiloxane, polyisoprene, styrene butadiene rubber, ethylene propylene diene monomer rubber, polychloroprene rubber, chlorosulfonyl polyethylene rubber, acrylonitrile butadiene rubber, polyacrylic rubber, ethylene acrylic rubber, epichlorohydrin rubber, polyisobutylene rubber, hydrogenated nitrile rubber, fluorocarbon rubber, fluorosilicone rubber, perfluorocarbon rubber, polyurethane, styrenic block copolymers, thermoplastic olefins, elastomeric alloys, thermoplastic copolyester, and/or thermoplastic polyamide.

The conducting particles within the conductor matrix may comprise one or a combination of the following constituents: Ag-coated glass particles, Ag-coated Cu particles, Ag-coated metal particles, Au-coated metal particles, copper microparticles, copper nanoparticles, silver microparticles, silver nanoparticles, nano-wires, metallic microparticles, nanotubes (e.g. carbon nanotubes), flakes (e.g. metallic flakes), graphene, aluminium microparticles, gold microparticles, tin microparticles, copper nanowires, silver nanowires, aluminium nanowires, gold nanowires, tin nanowires, copper flakes, silver flakes, aluminium flakes, gold flakes, tin flakes, carbon particles.

Preferably, the elongated elastic conductor comprises an elastic and compressible core and a conductive wire wrapped around the elastic core.

The elastic and compressible core preferably comprises an elongated body of natural rubber. The elastic and compressible core may comprise any element of the group consisting of natural rubber, elastane, polyurethane, silicone rubber, polyisoprene, polyethylene rubber, polyacrylic rubber, and thermoplastic polyurethane, and combinations thereof. The elastic and compressible core preferably has a diameter perpendicular to the direction of the elongation of the elastic and compressible core of 0.5 mm to 1.2 mm.

Preferably, the elastic and compressible core has a round cross section.

The conductive wire may comprise any element of the group consisting of copper, copper alloys, silver, stainless steel, aluminum, nickel, tin, zinc, cobalt, manganese, iron, gold, carbon and combinations thereof. Preferably, the conductive wire is silver-coated copper wire. The conductive wire preferably is a litz wire, e.g., made from 5-30 wires, each having a diameter of 0.02 mm-0.08 mm.

The elongated elastic conductor may comprise multiple conductive wires wrapped around the elastic core.

There may be specific wrapping or winding configurations. Preferably, the elongated elastic conductor comprises two conductive wires wound around the elastic core in opposite winding direction and with at least 5 windings/cm.

By providing an elongated elastic conductor with such a construction, the electrical conductor may have an improved elasticity and compressibility.

Preferably, the elongated elastic conductor further comprises a non-conductive yarn wrapped around the elastic core.

Preferably, the electrical wire or wires may be wrapped around the non-conductive yarn. Then, this construct may be wrapped around the elastic core.

Preferably, the conductor remains electrically conductive at a strain of at least 50%, more preferably at least 75% and most preferably at least 100%. In its unstretched state, the conductor preferably has a resistance between 1 Ω/m and 100 Ω/m. Preferably, when stretched to a strain of 30% the resistance of the stretched conductor increases by a factor of less than 10, preferably less than 5, and more preferably less than 2.

Consequently, it is preferred that the elongated elastic seam tape can be elastically stretched to a strain of at least 50%, preferably to at least 75% and more preferably to at least 100%.

Preferably, the lumen has a first cross-sectional area (perpendicular to the length extension) and the conductor has a second cross-sectional area (perpendicular to the length extension), wherein the ratio between the first and second cross-sectional areas is at least 1.4, preferably at least 2.0, more preferably at least 5.0. These ratios can be measured by simply cutting the elongated elastic seam tape perpendicularly to the length extension, taking an image of the cut cross-section and evaluating the area occupied by both the conductor and the lumen by means of, e.g., image analysis. In this context, it is to be noted that the first cross-sectional area encompasses the second cross-sectional area, i.e. the area covered by the conductor is considered to be part of the lumen area. Moreover, it is to be noted that the lumen may of course be compressed by applying pressure and/or during the cutting process. Yet, the ratios mentioned above refer to the fully expanded lumen in its steady state, which may, e.g., be achieved by filling the lumen with air at ambient pressure.

The lumen has a width defined as the average distance perpendicular to the length extension and parallel to the extension of the first and second layers measured between the two points where the first and second layers contact each other and are bonded to each other. The ratio between this width and the diameter of the conductor is preferably at least 1.5, more preferably at least 2.5 and most preferably at least 4.

At the interface between the first and second layers, a first area is defined as the area over which the first and second layers are bonded to each other and a second area is defined as the area where the first and second layers are not bonded to each other. The ratio between the first and second areas is preferably smaller than 4, more preferably smaller than 3 and most preferably smaller than 0.67.

It is important to note that the first and second layers having a conductor disposed therebetween may be part of a larger laminate structure with one or more additional layers. Accordingly, the first and/or second layer may constitute the top and/or bottom layer of the elongated elastic seam tape. Alternatively, one or more additional layers are provided above the first layer and/or one or more additional layers are provided below the second layer. Consequently, the first and second layers may be formed of different materials depending on whether or not they form an outermost layer or an intermediate layer within the elongated elastic seam tape.

It is, however, generally preferred that the second layer comprises an adhesive material which allows for bonding the second layer to the first layer. Preferred adhesive materials are polyurethanes, polypropylenes, polyethylenes, polyamides, polyesters, polyolefins and silicones. It is preferred that the adhesive material is an elastic polymer, preferably a thermoplastic elastic polymer. One particularly preferred example material is a thermoplastic low-melting-temperature polyurethane having a melting point at a temperature between 80° C. and 120° C. Preferably, the adhesive property of the adhesive material can be activated by heat, light, pressure, and/or a chemical reaction. Preferably, the adhesive material has a melting temperature that allows for melting the material by applying ultrasonic energy, hot air, and/or hot lamination pressure.

The function role of the first layer may vary depending on the laminate structure. Accordingly, the first layer may comprise an elastic textile, and/or an elastic polymer and/or a thermoplastic elastic polymer. The first layer may also be made of the same adhesive material as the second layer. If the first layer forms the top layer of the seam tape, the first layer preferably comprises an elastic textile such as, for example, an elastane-based elastic ribbon, or an elastic polymer such as a silicone. The elastic textile may also comprise a mixture of elastane with other polymers such as, for example, polyester, polyamide or polypropylene.

If the first layer is an intermediate protective or insulation layer, the first layer preferably comprises an elastic polymer such as a thermoplastic high-melting-temperature polyurethane having a melting point, e.g., above 170° C. Other examples of suitable elastic polymers are polyurethanes, polypropylenes, polyethylenes, polyamides, polyesters, polyolefins, silicones and styrenic block copolymers.

Preferably, the melting point of the material of the first layer is higher than that of the material of the second layer. Thus, the second layer can be partially bonded to the first layer, e.g., by the application of heat without melting or deforming the first layer. This may also ensure that the conductor is not inadvertently bonded to the first layer during bonding of the second layer to the first layer and remains movable within the lumen. Of course, this can also be achieved by the first layer consisting of a material which does not melt at all. In the context of the present invention, such a material may be considered to be a material having an infinite melting temperature and, accordingly, also fulfils the requirement that the melting point of the material of the first layer is higher than that of the material of the second layer.

Preferably, the second layer can be peeled off of the first layer at least at one longitudinal end of the seam tape so as to expose a section of the conductor. Preferably, peeling off can be performed manually with a peel force of preferably less than 100 N. This functionality may be achieved by choosing suitable material combinations of the first and second layers and/or by partially laminating the first and second layers at a partial lamination temperature and a partial lamination pressure for a partial lamination time. For example, if the first layer comprises a polyurethane with a melting point of roughly 170° C. and the second layer comprises a polyurethane with a melting point of roughly 90° C., a partial lamination may be achieved by positioning the conductor between the first layer and the second layer and by pressing the first layer and the second layer together at a temperature of 90° C. and a pressure of 30 mbar for 20 seconds.

The first and/or second layer may also comprise one or more flaps or straps which allow for easily gripping each of the first and second layers and separating them from each other.

The present invention is not limited to seam tapes comprising a single conductor within a single lumen only. Rather, two or more lumina with two or more conductors may be provided within one and the same seam tape. For example, each longitudinal edge of the second layer may be bonded to a corresponding longitudinal edge of the first layer and one or more intermediate longitudinal sections of the second layer may be bonded to one or more corresponding intermediate longitudinal sections of the first layer so as to form two or more lumina extending along the entire length of the seam tape between the first and second layers. Preferably, at least three, more preferably at least four and most preferably at least five such lumina are provided by respective intermediate bonding sections. Preferably, each of said lumina comprises a separate elongated elastic conductor positioned movably therein. It is, however, not excluded that one or more of the lumina remain empty or receive an entity different from an electrical conductor. Preferably, the conductors in the various lumina are identical to each other. Yet, different types and/or sizes of conductors may be employed for the various lumina depending on the purpose of the conductor. For example, one conductor may be used to power a device, requiring a relatively large current, whereas another conductor may be used for data transfer, requiring a relatively low current.

While two or more lumina having respective conductors therein may be provided within a single plane disposed between the first and second layers as described above, different lumina may, additionally or alternatively, also be provided in different planes of the seam tape. For example, the seam tape may comprise an elongated elastic third layer, an elongated elastic fourth layer, partially bonded to the third layer, and a second elastic elongated conductor. Each longitudinal edge of the fourth layer may be bonded to a corresponding longitudinal edge of the third layer so as to form a second lumen extending along the entire seam tape between the third and fourth layers. The second conductor may be movably positioned within said second lumen. Of course, two or more lumina may also be provided between the third and fourth layers.

As mentioned above, the seam tape of the present invention may comprise various additional layers forming a stack or laminate. Accordingly, the third layer need not be directly adjacent to the second layer of the seam tape. Rather, one or more additional layers may be provided between the second layer and the third layer. For example, a protection or insulation layer may be provided between the second layer and the third layer.

However, the third layer can also be directly adjacent to the second layer. While the third layer may comprise a material different from the material of the second layer, the second and third layers may also be made from the same material. If the second and third layers are made from the same material and are positioned directly adjacent to one another, it may not be possible to distinguish between the second and third layer. In this case, the third layer may be integral with the second layer or, in other words, the third layer may be identical to the second layer. In other words, the seam tape according to this particular embodiment would comprise, in that order, the first layer, the first conductor, the second layer, the second conductor, and the fourth layer.

Of course, the concept of having conductors in different planes as explained above may be combined with the concept of having different conductors within one plane and/or may be extended to a concept of having conductors in multiple planes, for example in three, four, five or more planes.

In any of these embodiments, it is preferred that the bottom layer comprises an adhesive suitable for attaching the elongated elastic seam tape to a piece of fabric or garment. Said bottom adhesive layer may be covered or coated by a removable film such as a release film or release paper in order to protect the adhesive layer of the seam tape. Before use, the user removes said removable film in order to expose the adhesive and attaches the adhesive to the fabric or garment.

Preferably, the elongated seam tape comprises an electrical connector connected to one end of the conductor. This allows for electrically connecting any additional devices such as sensors or the like to the electrical conductor of the seam tape. Such an electrical connector may be provided on either or both sides of the seam tape. Preferably, the connector comprises a crimp sleeve attached to the end of the conductor and a connector element longitudinally protruding from the lumen of the seam tape. Thus, the connection between the conductor on the one hand and the connector via the crimp sleeve on the other hand may be located at least partly and preferably completely within the lumen, which also allows for sealing the electrical connection against external influences which may arise, for example, during washing of the garment or from sweat while wearing the garment. Moreover, the connector element longitudinally protruding from the lumen allows for easy electrical connection to any further devices or electronics without the need to introduce the respective connector or socket into the lumen which may be intricate and cumbersome. The electrical connection of the connector element to other devices or sensor components may be achieved by soldering and/or a mechanical contact. The connector element may comprise one or a combination of the following elements: a metal pin, a magnetic button, a solder pad, a printed circuit board, a conductive Velcro tape. In one preferred example, the connector element comprises a metal ring and a conductive rivet-type snap button connector with the rivet stud extending through the opening of the metal ring and thus electrically and mechanically contacting the metal ring.

Preferably, the conductor in its unstretched equilibrium state has a first length and the lumen in the unstretched equilibrium state of the seam tape has a second length, which is greater than the first length, wherein the crimp sleeve in the unstretched equilibrium state of the seam tape is preferably completely withdrawn into the lumen of the seam tape. In this state, the end of the crimp sleeve proximate to the respective end of the lumen has preferably a distance to said end of the lumen of at least 1 mm, preferably of at least 3 mm, more preferably of at least 5 mm. Preferably, the difference between the first length and the second length amounts to at least 2 mm, more preferably at least 3 mm and even more preferably at least 5 mm. As will be described in further detail below, such a seam tape with different first and second lengths may be achieved by providing the conductor during manufacturing of the seam tape in a pre-stretched configuration such that the pre-stretched conductor extends along the entire length of the lumen while the first and second layers are in their unstretched equilibrium state. Due to friction between the conductor and the inner surface of the lumen, the conductor remains in its pre-stretched state. However, when a segment of the seam tape is cut-off of a seam tape material, the pre-stretched conductor within the cut-off segment relaxes during and/or after cutting so that both ends of the relaxed conductor are completely withdrawn into the lumen. This happens due to the fact that the friction is reduced in case the cut-off segment is sufficiently short.

Preferably, the first and second layers comprise an adhesive (wherein the adhesive material of the first and second layers may be different). In this case, the lumen may be sealed by the connector element and the adhesive layers surrounding the connector element. In other words, at least a portion of the connector element is preferably introduced into the lumen and the adhesive inner surface of the lumen is used to connect the material of the first and second layers in a sealing manner around the connector element. Thus, the conductor as well as its connection to, e.g., the crimp sleeve of the connector can be completely sealed within the lumen of the seam tape. Accordingly, the amount of water or humidity which can reach these electrical components during, e.g., washing or wearing the fabric or garment in the rain, is minimized. Again, such a seal by means of the connector element may be provided on either or both ends of the elongated seam tape. However, one of the ends of the seam tape may also be sealed by different means.

The present invention further relates to a fabric comprising the elongated seam tape described above bonded thereto. The fabric may be a fabric the use of which may benefit from the provision of one or more electrical conductors. The fabric may, for example, be a garment such as a sports suit, an electro muscle stimulation suit (EMS suit), or a garment with means to electronically measure biological signals such as muscle activity, heart activity or breathing, or a garment with means to electronically measure environmental parameters which may be safety relevant, such as temperature, radiation levels, pressure. Preferably, the seam tape is adhesively bonded to a surface of the fabric. For example, the adhesive material of the second layer may be used to adhesively bond the seam tape to the fabric. However, if additional layers are present below the second layer, as outlined above, another (outermost) adhesive layer may be used to adhesively bond the seam tape to the fabric.

Bonding the seam tape to the fabric may be achieved by applying heat and/or pressure to the seam tape being properly positioned on the fabric. Depending on the material combination of the various layers of the seam tape, said application of temperature and/or pressure may also induce an increase of the bond between the first and second layers. Thus, the lumen between the first and second layers of the seam tape being bonded to the fabric may be smaller than the lumen of the seam tape before bonding. In certain instances, the lumen may even be completely closed during said additional bonding process.

Preferably, the crimp sleeve of the connector is adhesively bonded to the first and/or second layer of the seam tape and/or to the fabric. If the crimp sleeve is completely withdrawn into the lumen of the seam tape as discussed above, the crimp sleeve is preferably only bonded to either or both of the first and second layers. If both the first and second layers comprise an adhesive material, bonding the seam tape to the fabric may at the same time lead to adhesive bonding of either or both of the first and second layers to the crimp sleeve. If sealing is not achieved by the connector element, as discussed above, sealing may also be achieved by simply closing the lumen around the crimp sleeve by means of bonding the first and second layers to the crimp sleeve.

If the crimp sleeve or a portion thereof protrudes from the lumen, it is preferred that the crimp sleeve is either directly or indirectly adhesively attached to the fabric as well.

Preferably, a reinforcement layer such as a textile reinforcement layer is provided, which is preferably also adhesively bonded to the fabric. The reinforcement layer is supposed to mechanically stabilize fixation of one or more of the layers of the seam tape and/or the connector to the fabric. Such a reinforcement layer may be provided at different positions. For example, a reinforcement layer may be provided on the top layer (opposite to the side of the seam tape bonded to the fabric) and may be adhesively attached to said top layer and/or the crimp sleeve and/or the connector element and/or the fabric. Alternatively or in addition, the reinforcement layer may be provided between the layer of the seam tape bonded to the fabric and the fabric. For example, a reinforcement layer may be partially incorporated into the adhesive layer of the seam tape bonded to the fabric. At the same time, said reinforcement layer protrudes beyond the end of the seam tape and may be adhesively bonded to the fabric at a position beyond the seam tape and/or to the connector element. Preferably, the reinforcement layer is more rigid than the seam tape material, so as to form a "rigid island" in the connector area. This can be achieved, for example, by choosing a reinforcement layer material which is significantly less stretchable than the fabric, or by choosing a reinforcement layer which is not stretchable by manual forces. Preferably, the reinforcement layer has a Young's modulus greater than 100 MPa, more preferably greater than 1 GPa.

Alternatively or in addition, the reinforcement layer may be provided to the side of the fabric opposite to the fabric's side to which the seam tape is bonded. In this case, the reinforcement layer may be adhesively bonded to only this opposite side of the fabric or may be adhesively bonded to both the fabric and a part of the connector element.

Accordingly, a cross section through the fabric and the seam tape perpendicular to the length extension of the seam tape may show one of the following layered structures, wherein "X" stands for one or more arbitrary layers:
- fabric-adhesive-crimp sleeve and conductor-adhesive-X-adhesive-reinforcement layer
- fabric-adhesive-X-adhesive-crimp sleeve and conductor-adhesive-X-adhesive-reinforcement layer
- fabric-adhesive-reinforcement layer-adhesive-crimp sleeve and conductor-adhesive-X
- fabric-adhesive-reinforcement layer-adhesive-crimp sleeve and conductor-adhesive-X-adhesive-reinforcement layer
- reinforcement layer-adhesive-fabric-adhesive-crimp sleeve and conductor-adhesive-X-adhesive-reinforcement layer.

Moreover, a cross section through the fabric and the connector element may comprise, in this order, the following layered structures:
- part of connector element-fabric-part of connector element-adhesive-reinforcement layer
- part of connector element-fabric-adhesive-reinforcement layer-part of connector element
- part of connector element-fabric-adhesive-reinforcement layer-adhesive-part of connector element-adhesive-reinforcement layer
- part of connector element-reinforcement layer-adhesive-fabric-part of connector element-adhesive-reinforcement layer.

BRIEF SUMMARY

The present invention further relates to a method of manufacturing an elongated elastic seam tape as described above. The method comprises providing first and second elongated elastic layers and an elongated elastic conductor positioned between the first and second layers. Each longitudinal edge of the second layer is then bonded to a corresponding longitudinal edge of the first layer such that a lumen extending along the entire seam tape between the first and second layers is formed and such that the conductor extends along and within said lumen.

Preferably, the first layer has a first melting temperature higher than a second melting temperature of the second layer. Preferably, bonding takes place at a temperature between the first and second temperatures. For example, bonding may be achieved at a temperature of 95° C. at a pressure of 100 mbar being applied for 20 s. This can be done, e.g., in a stationary hot press. Accordingly, the layers are pressed together and heated and then removed from the press. Alternatively, manufacturing may take place in a continuous manner. For example, the first and second layers and the conductor may be fed between two rolls of a seam taping machine which are heated and pressed together. Thus, a continuous elongated seam tape may be manufactured under constant and controlled conditions. Alternatively, heat and pressure may only be applied to those areas where bonding between the first layer and the second layer is desired, e.g. by employing rolls containing grooves in the lumen area.

As discussed above, the conductor may be provided in a pre-stretched configuration with the pre-stretched conductor extending along the entire length of the lumen while the first and second layers are in their unstretched equilibrium state. In this context, "pre-stretched" refers to a conductor which has a length corresponding to at least 101% of its equilibrium length in the unstretched state, preferably to a conductor which has a length corresponding to at least 103% of its equilibrium length in the unstretched state, and more preferably to a conductor which has a length corresponding to at least 105% of its equilibrium length in the unstretched state. The first and second layers are then partially bonded to each other with the conductor remaining in its pre-stretched condition. As explained above, the conductor remains in its pre-stretched condition once manufacturing is completed due to friction forces between the conductor and the inner surfaces of the lumen. A segment of the seam tape to be applied to a piece of fabric is then cut off of the continuous seam tape material (provided, for example, in the form of a roll). At that point, the pre-stretched conductor within the cut-off segment relaxes during and/or after cutting so that both ends of the relaxed conductor are completely withdrawn into the lumen of the seam tape. This happens because the friction forces between the conductor and the inner surfaces of the lumen are reduced in case of a seam tape segment having reduced length.

If further layers such as protective insulation layers are needed, these are added in additional steps or at the same time using the same techniques as those discussed above for laminating the first and second layers to each other. The layers may be added and laminated sequentially or they can be laminated at the same time.

BRIEF DESCRIPTION OF THE DRAWINGS

Preferred embodiments of the present invention are further elucidated below with reference to the figures, which show.

DETAILED DESCRIPTION

Figure 1:
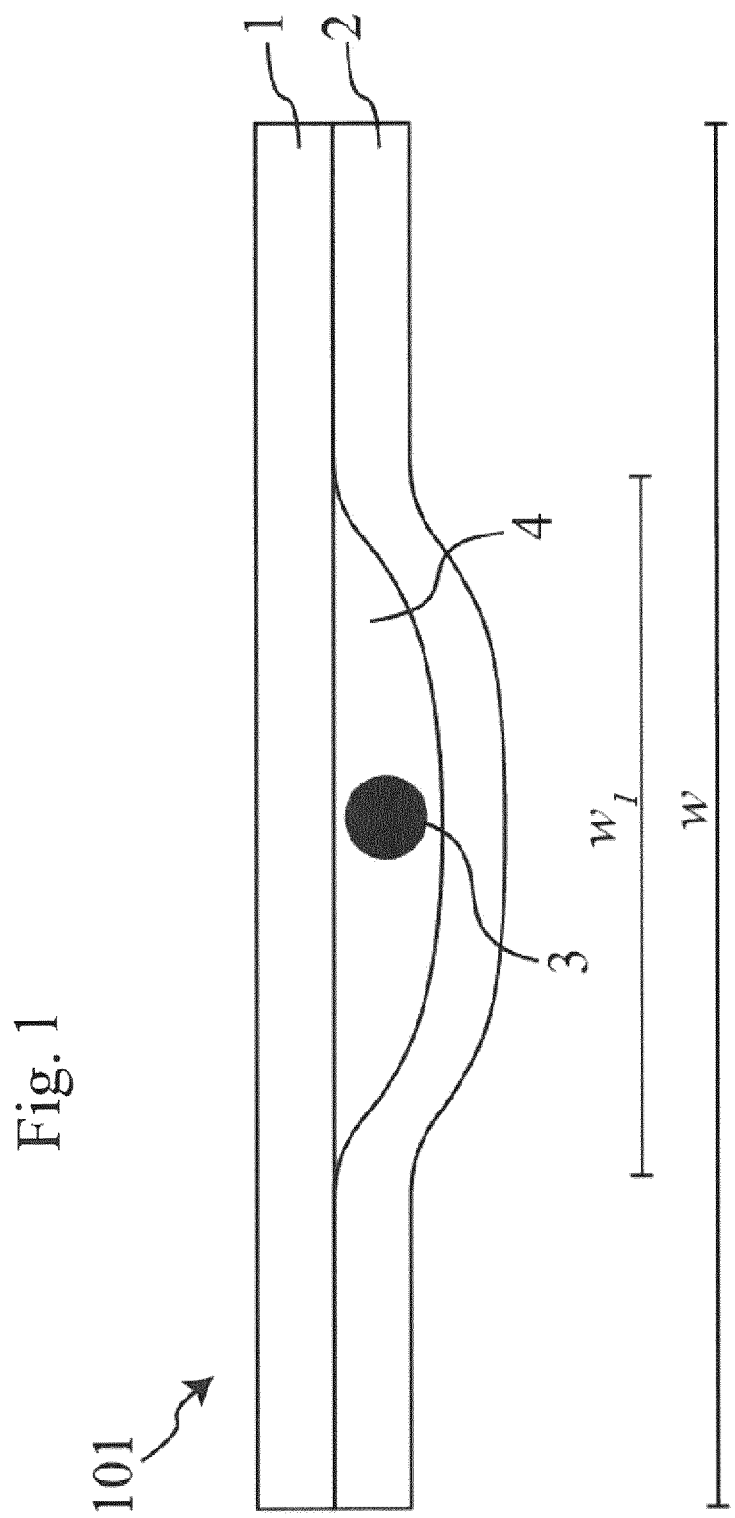
FIG. 1 a cross section through a preferred embodiment of a seam tape according to the present invention.

FIG. 1 shows a cross section (perpendicular to the longitudinal extension of the seam tape) through a preferred embodiment of an elongated elastic seam tape 101 according to the present invention. The seam tape 101 comprises an elongated elastic first layer 1 consisting of, e.g., a textile tape or a plastic film, and an elongated elastic second layer 2 consisting of an adhesive material such as a thermoplastic elastic polymer (or thermoplastic elastomer). As schematically shown in FIG. 1, each longitudinal edge of the second layer 2 (corresponding to the left and right edges in the cross section shown) is bonded to a corresponding longitudinal edge of the first layer 1 so as to form a lumen 4 extending along the entire seam tape between the first and second layers. An electrical conductor 3 is movably positioned within said lumen 4.

Figure 22:
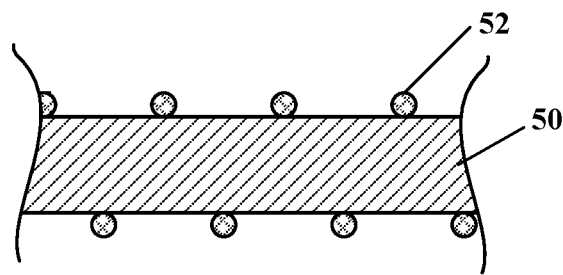
FIG. 22 a longitudinal section through a preferred embodiment of an elongated elastic conductor according to the present invention.

Preferably, the elongated elastic conductor comprises an elastic and compressible core 50 and a conductive wire 52 wrapped around the elastic core, as illustrated in FIG. 22.

The tape may generally have any dimensions suitable for its use. Typically, the width of the tape (corresponding to the left-right-extension in FIG. 1) is between 5 mm and 5 cm, preferably between 5 mm and 1 cm and more preferably between 6 mm and 11 mm. The thickness of the seam tape depends on the number of layers (see the subsequent embodiments) but is generally between 0.5 mm and 1 cm, preferably between 0.8 mm and 5 mm. In general, however, the thickness of the seam tape will vary along its width since the thickness at the position of the conductor will be greater than the thickness of the rest of the tape as schematically shown in FIG. 1. Typically, the thickness of the top layer is between 0.2 mm and 3 mm, the thickness of the insulation layers is between 0.02 mm and 2 mm and the thickness of the adhesive layers is between 0.02 mm and 2 mm. The length of the elongated elastic seam tape is preferably greater than 0.3 m, more preferably greater than 0.5 m, even more preferably greater than 2 m, and most preferably greater than 10 m. The elongated elastic seam tape of such a length may, e.g., be provided in the form of a roll. Before use, the user cuts off a segment of the elongated elastic seam tape in accordance with his needs.

Of course, the skilled person will understand that the shape and relative dimensions of the components of the seam tape as shown in FIG. 1 are merely schematic in nature and that, e.g., the cross section of the first layer 1 need not be rectangular and that the conductor need not be cylindrical. Moreover, the lumen 4 may have different shapes and sizes deviating from the schematic drawing shown in FIG. 1, which apparently will also have an influence on the shape and curvature of the second layer 2.

It is, however, preferred that the ratio between the cross-sectional area of the lumen and the cross-sectional area of the conductor is at least 1.4, preferably at least 2, more preferably at least 5. In the embodiment shown in FIG. 1, said ratio is greater than 5. The distance between the two points where the first and second layers start to be bonded to each other, measured perpendicular to the length extension defines a width $w_1$ of the lumen, see FIG. 1. The ratio between said width $w_1$ and the width w of the seam tape is preferably larger than 0.2, preferably larger than 0.4 and more preferably larger than 0.6.

Figure 2:
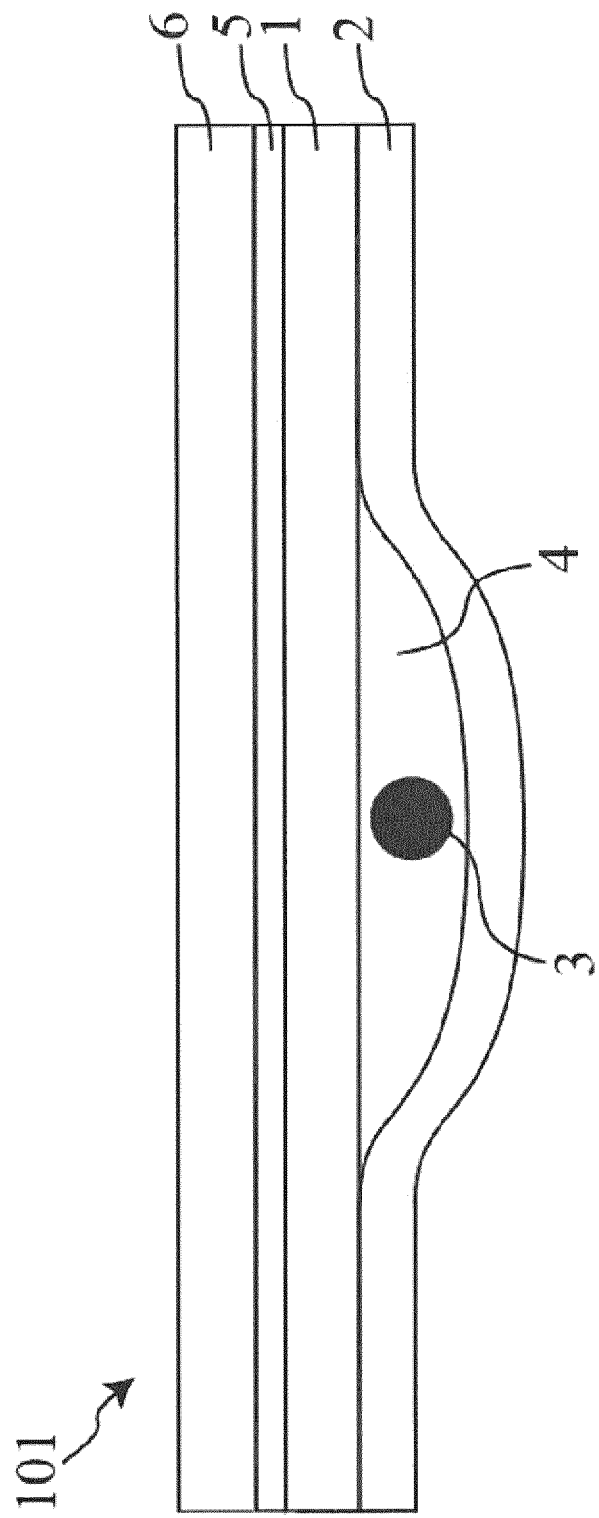
FIG. 2 a cross section through a preferred embodiment of a seam tape according to the present invention.
Figure 3:
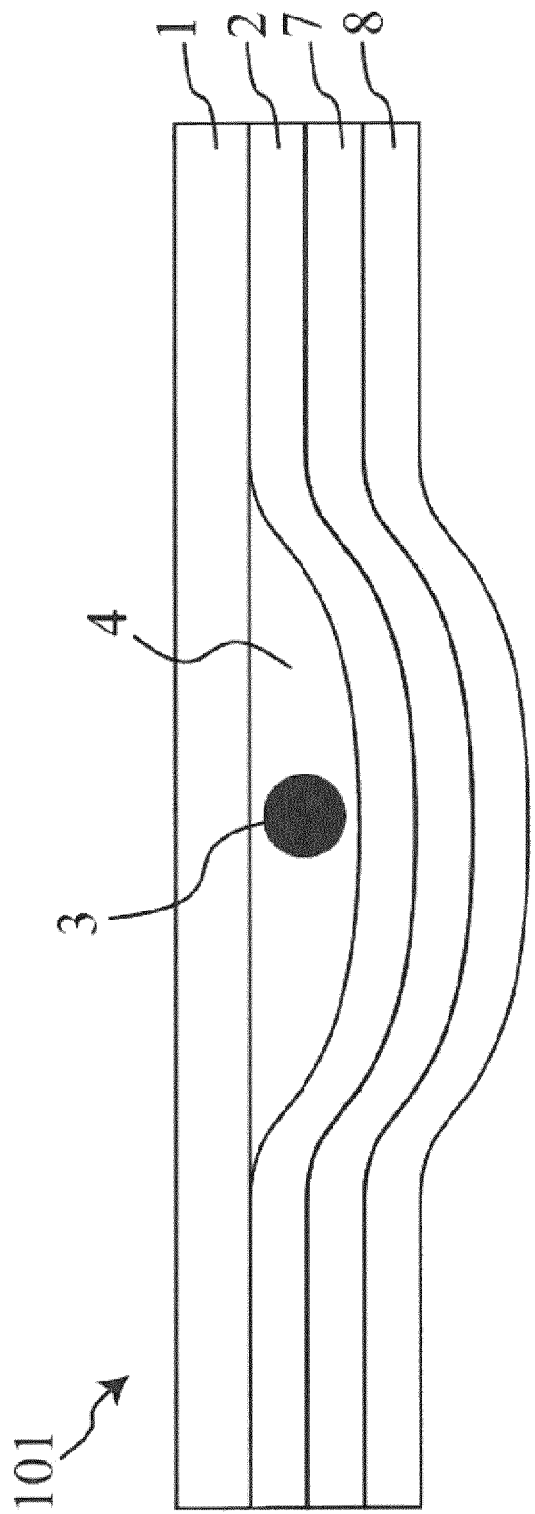
FIG. 3 a cross section through a preferred embodiment of a seam tape according to the present invention.
Figure 4:
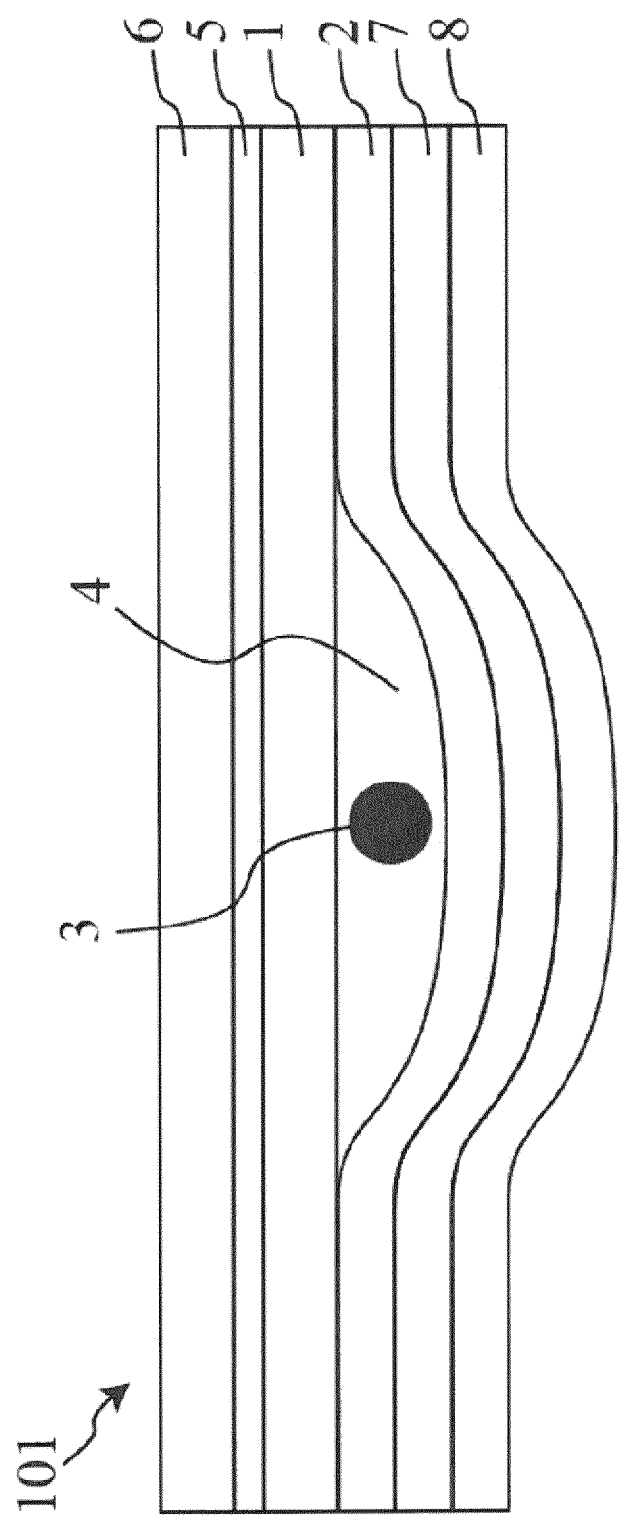
FIG. 4 a cross section through a preferred embodiment of a seam tape according to the present invention.

As mentioned above, the seam tape 101 of the present invention may comprise one or more additional layers on either or both of the first and second layers. Some exemplary embodiments comprising such additional layers are shown in FIGS. 2 to 4. For example, a textile tape or a plastic film 6 may be bonded to the first layer 1 by means of an additional adhesive layer 5 as shown in FIG. 2. Alternatively, an additional protective or insulation layer 7 may be provided adjacent to the second layer 2 as shown in FIG. 3. Said protective or insulation layer 7 may comprise an elastic polymer such as a thermoplastic high-melting-temperature polyurethane having, e.g., a melting point above 170° C. Since the protective or insulation layer 7 does not necessarily comprise an adhesive material, an additional adhesive layer 8 may be foreseen for bonding or attaching the seam tape to a fabric as discussed further below.

Of course, the additional layers 5 and 6 shown in FIG. 2 as well as the additional layers 7 and 8 shown in FIG. 3 may be provided in one and the same embodiment as shown in FIG. 4.

As discussed above, two or more elongated elastic conductors may be provided within the inventive seam tape. For example, two or more conductors may be provided within one plane of the seam tape, i.e. between the same adjacent layers 1 and 2 as shown in the embodiments of FIGS. 5 to 8.

Figure 5:
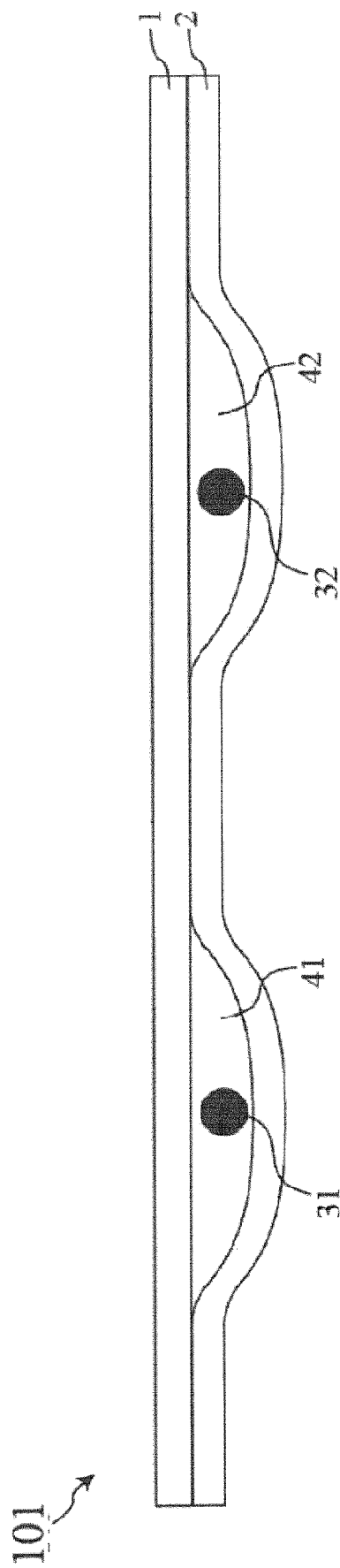
FIG. 5 a cross section through a preferred embodiment of a seam tape according to the present invention.

In the seam tape 101 according to the embodiment of FIG. 5, each longitudinal edge of the second layer 2 is bonded to a corresponding longitudinal edge of the first layer 1 (similar to the embodiment shown in FIG. 1) and one intermediate longitudinal section of the second layer is bonded to one corresponding intermediate longitudinal section of the first layer so as to form two lumina 41 and 42 extending along the entire seam tape between the first and second layers. In each of the lumina 41 and 42, an elongated elastic conductor 31, 32 is movably positioned. Of course, this concept may be extended to three or more lumina containing three or more conductors by providing further intermediate sections analogously to the embodiment shown in FIG. 5.

Figure 6:
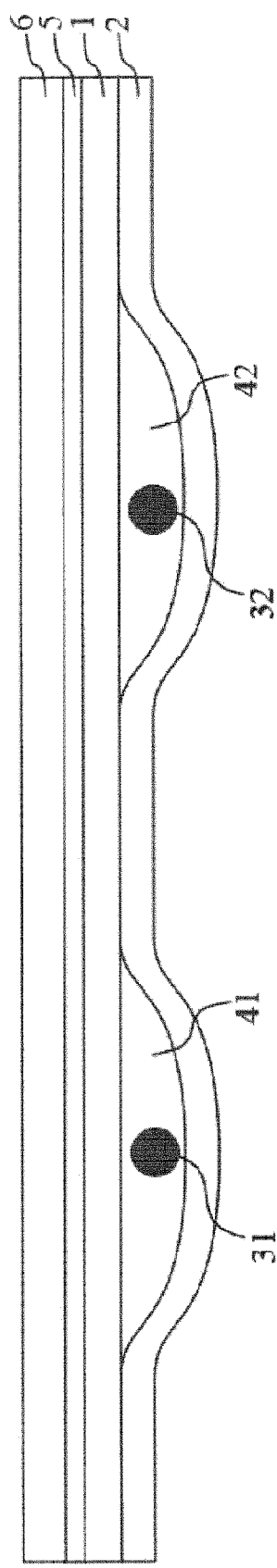
FIG. 6 a cross section through a preferred embodiment of a seam tape according to the present invention.
Figure 7:
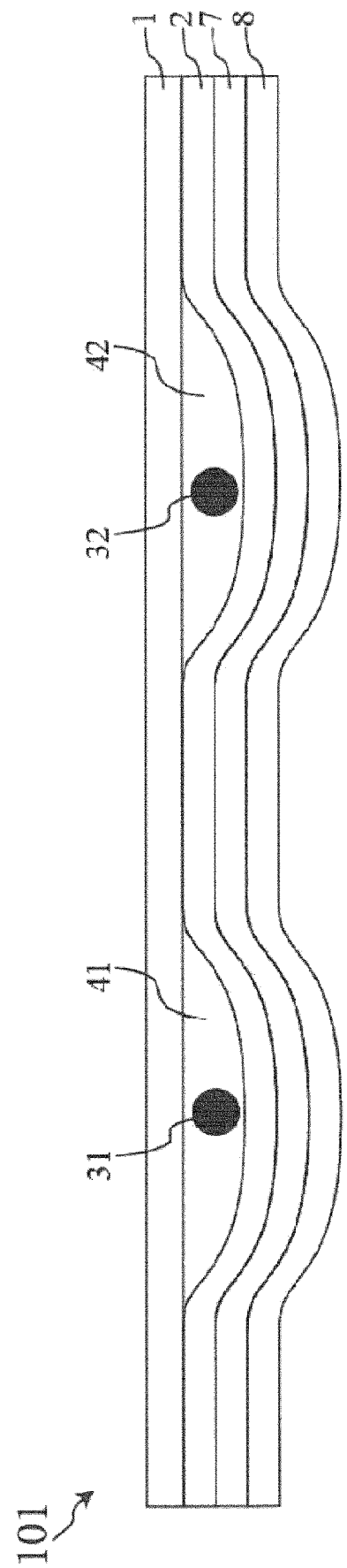
FIG. 7 a cross section through a preferred embodiment of a seam tape according to the present invention.
Figure 8:
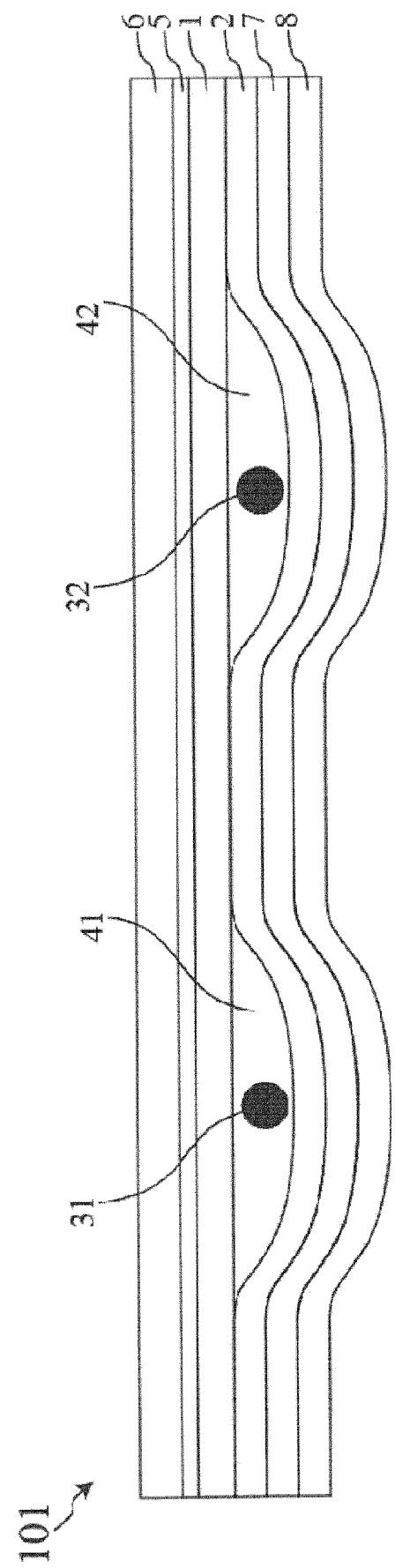
FIG. 8 a cross section through a preferred embodiment of a seam tape according to the present invention.

FIGS. 6 to 8 show preferred embodiments of a seam tape 101 having a layered structure corresponding to those of FIGS. 2 to 4, however, with the presence of two lumina containing two conductors analogously to the embodiment shown in FIG. 5.

Figure 9:
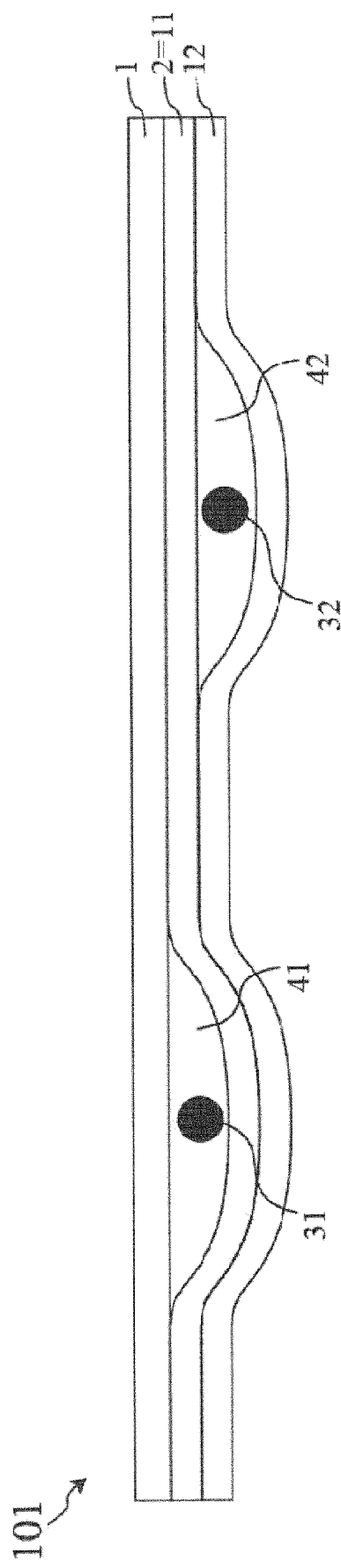
FIG. 9 a cross section through a preferred embodiment of a seam tape according to the present invention.
Figure 10:
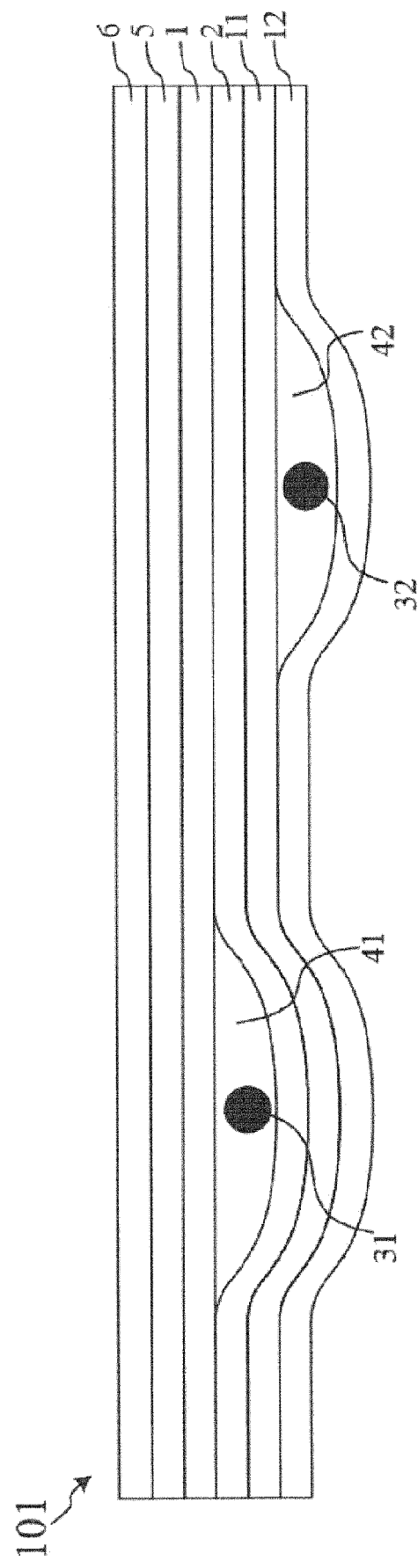
FIG. 10 a cross section through a preferred embodiment of a seam tape according to the present invention.
Figure 11:
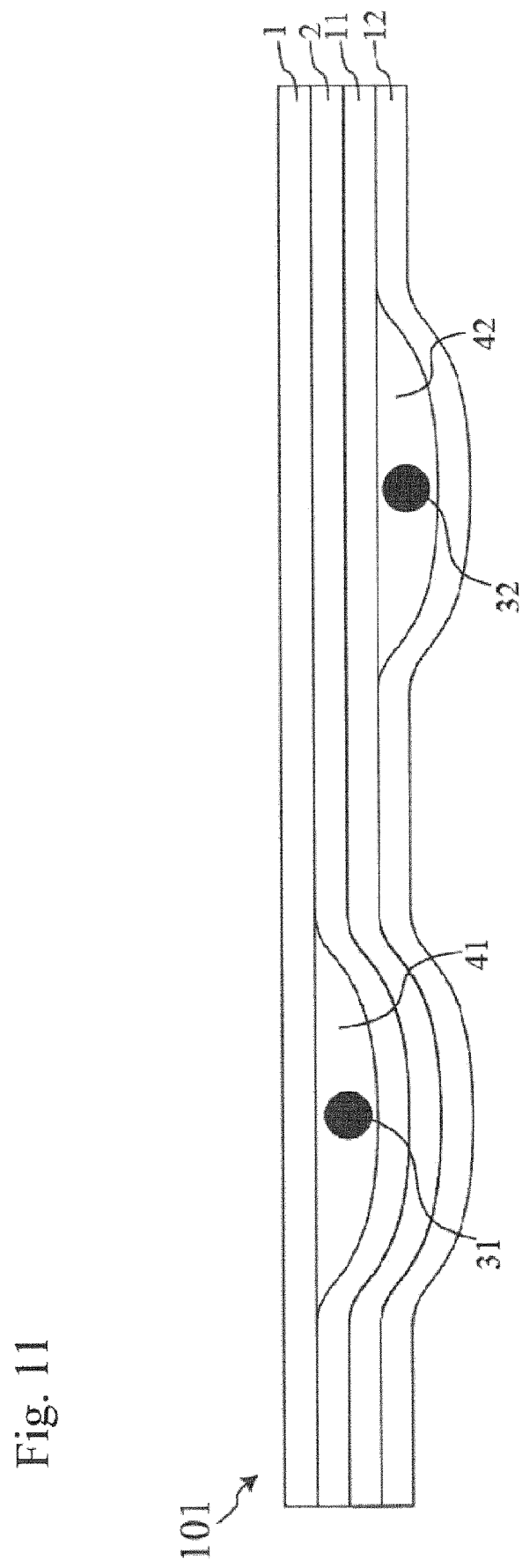
FIG. 11 a cross section through a preferred embodiment of a seam tape according to the present invention.
Figure 12:
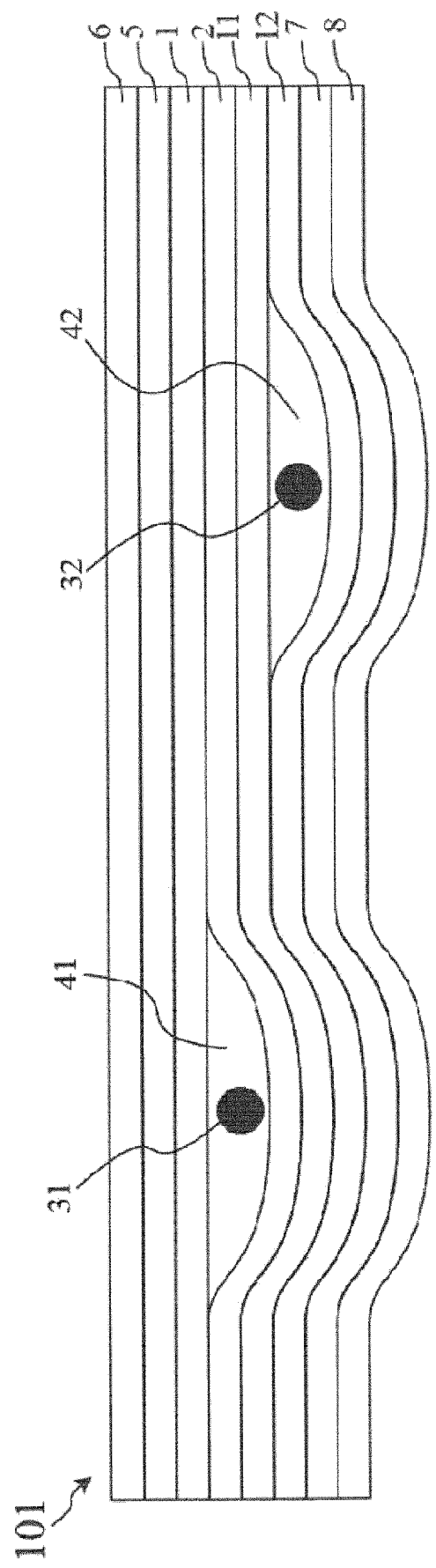
FIG. 12 a cross section through a preferred embodiment of a seam tape according to the present invention.

Alternatively or in addition, another conductor may be provided in a different plane of the seam tape. For example, the seam tape 101 according to the embodiment shown in FIG. 10 comprises an elongated elastic third layer 11 and an elongated elastic fourth layer 12, partially bonded to the third layer 11, wherein each longitudinal edge of the fourth layer 12 is bonded to a corresponding longitudinal edge of the third layer 11 so as to form a second lumen 42 extending along the entire seam tape between the third and fourth layers. A second elastic elongated conductor 32 is movably positioned within said second lumen 42. In addition, the seam tape of FIG. 10 comprises another adhesive layer 5 and a textile tape or plastic film 6. In the embodiment shown in FIG. 10 (and similarly in the embodiments in FIGS. 11 and 12, respectively), the third layer 11 is different from the second layer 2. However, as shown in FIG. 9, the third layer 11 may also be integral with the second layer 2. While the third layer 11 in all embodiments shown in FIGS. 10 to 12 is immediately adjacent to the second layer 2, one or more additional intermediate layers may be provided between the second layer 2 and the third layer 11.

In all embodiments shown in FIGS. 1 to 12, the lumen 4 (or the lumina 41 and 42) is positioned such as to create a bulge in the second layer 2 (and/or the fourth layer 12). In other words, the surface of the first layer 1 being adjacent to the second layer 2 is substantially planar and appears not to be affected by the presence of the lumen 4, 41, 42, whereas the second layer is curved or bent so as to accommodate the lumen between the first and second layers.

Figure 13:
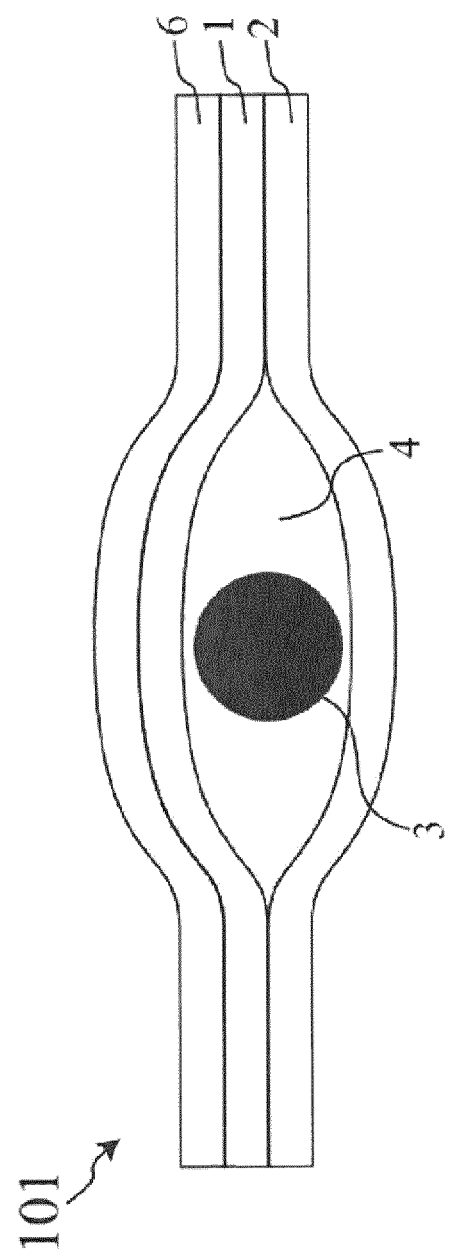
FIG. 13 a cross section through a preferred embodiment of a seam tape according to the present invention.

It is, however, also an option that the lumen 4 (or the lumina 41 and 42) is somewhat symmetrically disposed between the first and second layers as shown, for example, in FIG. 13. In this case, both the first layer 1 and the second layer 2 are curved or bent along the width direction of the seam tape so as to accommodate the lumen 4, 41, 42 therebetween. Such a symmetrically positioned lumen 4 can, for example, be achieved if the material of both layers 1 and 2 comprises an adhesive such as a thermoplastic elastic polymer, which material is then deformed during bonding. While the adhesive material of the layers 1 and 2 need not be identical, a symmetrical arrangement of the lumen 4 between the layers 1 and 2 is most easily achieved if the adhesive materials of the first layer 1 and the second layer 2 have a comparable melting temperature.

By contrast, an asymmetrical positioning of the lumen 4 as shown, for example, in FIG. 1 may be most easily achieved if the melting temperature of the first layer is substantially higher than the melting temperature of the second layer. In this case, only the material of the second layer 2 is deformed during bonding, whereas the first layer 1 remains effectively unaffected by the temperature and pressure applied during bonding.

Figure 14:
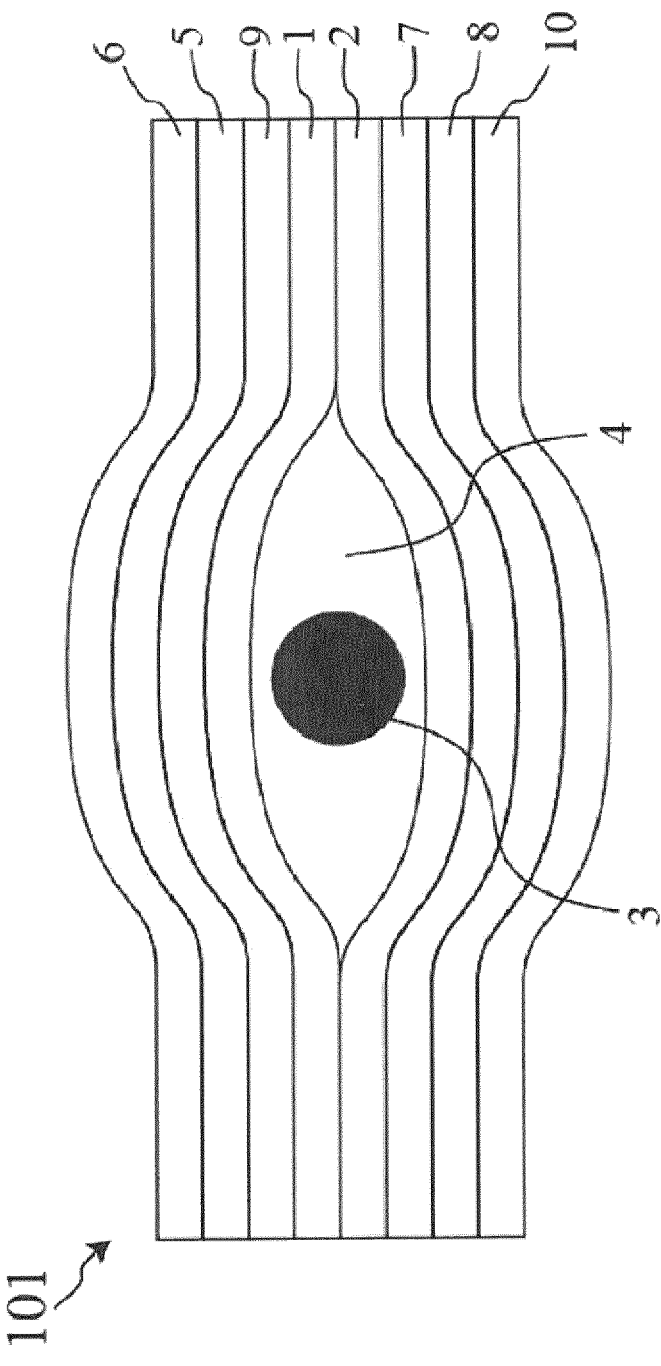
FIG. 14 a cross section through a preferred embodiment of a seam tape according to the present invention.

FIG. 14 shows a further preferred embodiment of the inventive seam tape 101 with a lumen 4 similar to that shown in FIG. 13. The first layer 1 and the second layer 2 also in this case comprise an adhesive material. On top of the first layer, a protective or insulation layer 9, another adhesive layer 5 and a top layer 6 are provided. Below the second layer 2, a further protective or insulation layer 7, a further adhesive layer 8 and removable film such as a release paper 10 are provided. The preferred embodiment of FIG. 14 provides an improved protection for the conductor, thanks to the protective insulation layers 9 and 7 which surround the conductor.

Figure 15:
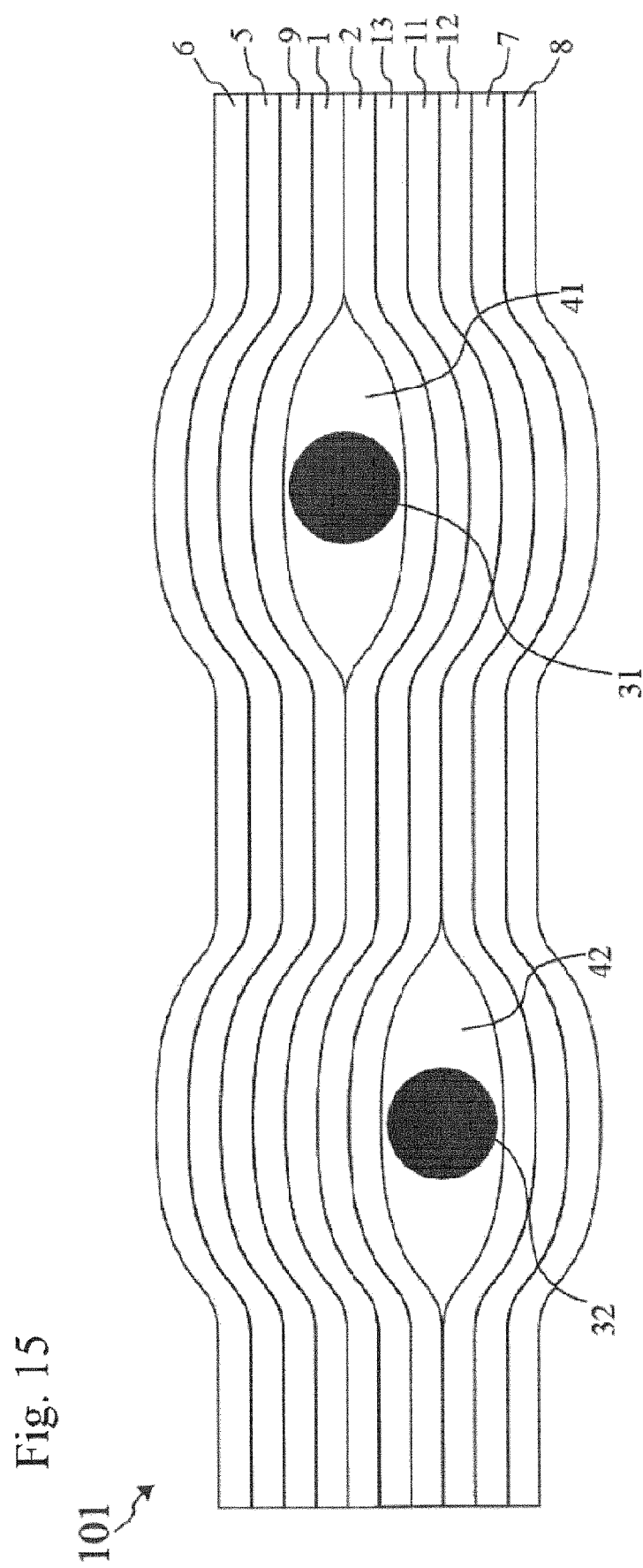
FIG. 15 a cross section through a preferred embodiment of a seam tape according to the present invention.

FIG. 15 shows a further preferred embodiment of the inventive seam tape 101 with two lumina 4 being present on different levels or planes of the laminate. A first lumen 41 is provided between adhesive first and second layers 1 and 2 and a second lumen 42 is provided between adhesive third and fourth layers 11 and 12. Between the second layer 2 and the third layer 11, a protective or insulation layer 13 is provided. Moreover, the seam tape 101 comprises a protective or insulation layer 9, an adhesive layer 5 and a textile tape or plastic film 6 on top of the first layer 1 and a protective or insulation layer 7 and an adhesive layer 8 below the fourth layer 12. Of course, a removable film (not shown) may be provided similar to the embodiment shown in FIG. 14. The preferred embodiment of FIG. 15 provides an improved protection for each of the conductors 31, 32, thanks to the protective insulation layers 9, 13 and 7 which surround the conductors. Furthermore, the preferred embodiment of FIG. 15 provides optimal insulation between the conductors, thanks to the protective insulation layer 13 separating the conductors.

FIGS. 16 to 19 show various embodiments of a fabric 20 comprising an elongated seam tape according to the present invention bonded thereto. While all embodiments shown in FIGS. 16 to 19 are based on a seam tape as shown in FIG. 13 comprising two adhesive layers 1 and 2 with the conductor 3 disposed therebetween and a top layer 6 (comprising a textile tape or a plastic film), it should be evident that all features shown in FIGS. 16 to 19 may be analogously applied for all other embodiments showing different seam tapes.

The elongated seam tape shown in the embodiments of FIGS. 16 to 19 all comprise an electrical connector connected to one end of the conductor 3. The electrical connector comprises a crimp sleeve 21 attached to the end of the conductor and a connector element 22 longitudinally protruding from the lumen of the seam tape. While the specific connector element 22 shown in FIGS. 16 to 19 comprises a rivet stud 22*a*, a metal ring 22*b* and a snap button 22*c*, other connector elements may be used in combination with the inventive seam tape. For example, the snap button 22*c* may be replaced with a magnetic button.

Figure 20:
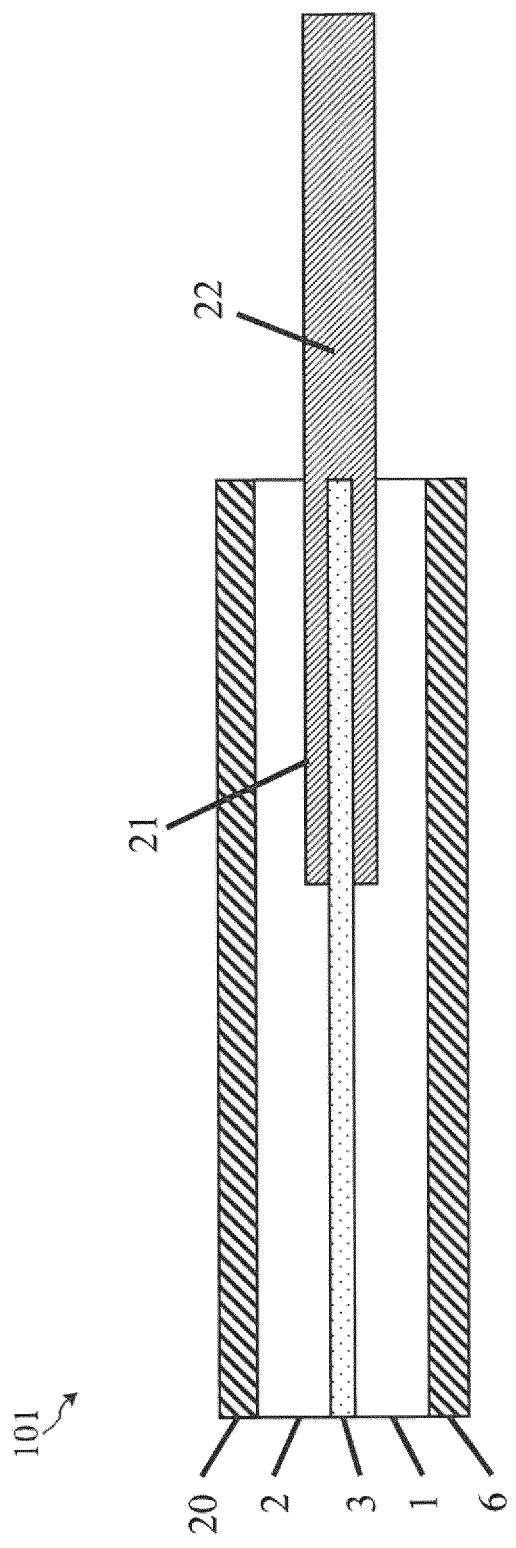
FIG. 20 a longitudinal section through a preferred embodiment of a seam tape with a connector according to the present invention.

Moreover, the seam tape of the present invention may also comprise a connector without any fabric being present. A preferred embodiment of such a seam tape 101 is shown in FIG. 20. The conductor 3 of the seam tape is mechanically and electrically connected to a crimp sleeve 21 and the crimp sleeve is connected to a connector element 22 protruding out of the lumen of the seam tape in the longitudinal direction.

In the embodiment shown in FIG. 20, the first and second layers 1 and 2 comprise an adhesive material and the conductor 3 is sealed from the environment by the adhesive material completely surrounding the crimp sleeve 21. In the embodiment shown in FIG. 20, the end of the crimp sleeve 21 proximate to the corresponding end of the seam tape 101 is flush with the end of the first and second layers 1 and 2 with the connector element 22 starting at the very end of the lumen of the seam tape.

Figure 21:
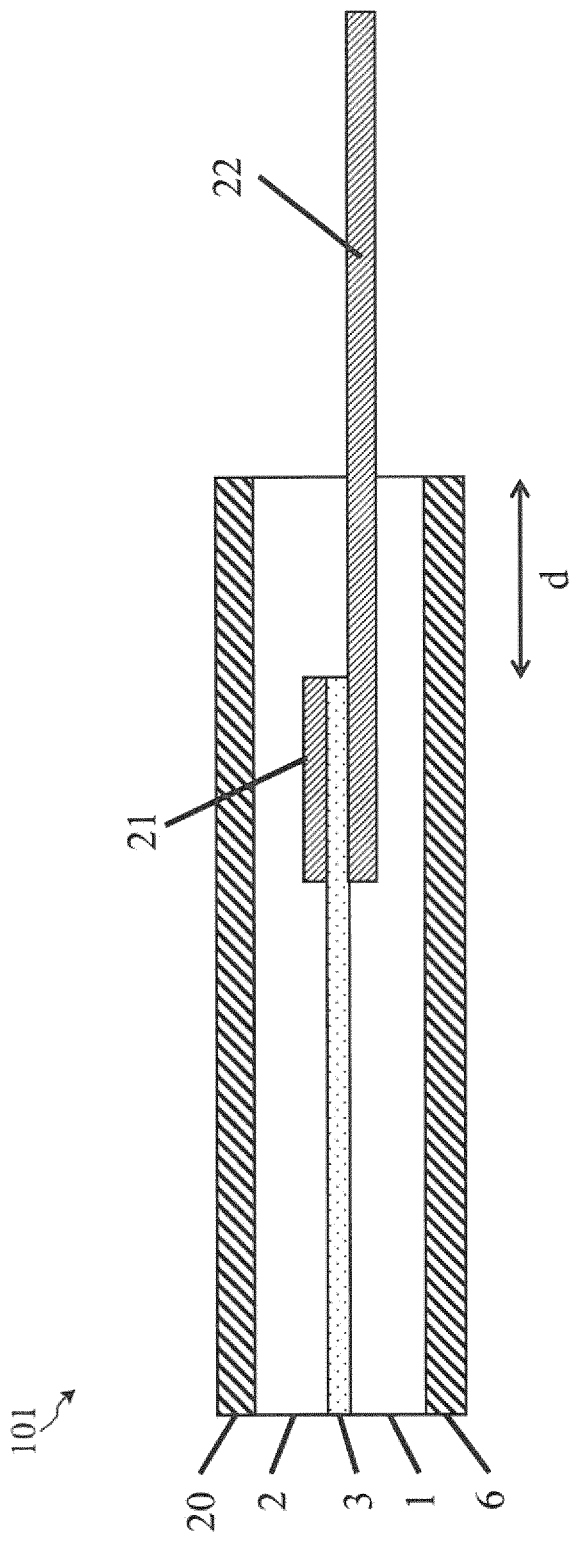
FIG. 21 a longitudinal section through a preferred embodiment of a seam tape with a connector according to the present invention.

FIG. 21 shows an alternative embodiment of the inventive seam tape 101 with a connector, where a portion of the connector element 22 is positioned within the lumen of the seam tape and where the crimp sleeve 21 is thus completely retracted into the lumen, which may then be sealed by the connector element and the adhesive layers 1 and 2 surrounding the connector element. Advantageously, the connection between the conductor 3 and the crimp sleeve 21 is thereby completely embedded in the seam tape, providing improved sealing as well as mechanical and electrical stability.

Preferably, the end of the crimp sleeve 21 proximate to the respective end of the lumen 4 has a distance d to said end of the lumen of at least 1 mm, preferably of at least 3 mm, more preferably of at least 5 mm. In case of a longitudinally symmetric placement of the conductor 3 within the lumen 4, said distance d corresponds to one half of the difference between the lengths of the lumen and the conductor.

In the embodiments shown in FIGS. 16 to 19, the first and second layers 1 and 2 comprise an adhesive material and the lumen is sealed by the adhesive material completely surrounding the crimp sleeve 21. In an alternative embodiment (similar to FIG. 21), a portion of the connector element 22 may be positioned within the lumen, which may then be sealed by the connector element and the adhesive layers surrounding the connector element.

Moreover, in all embodiments shown in FIGS. 16 to 19, the adhesive material of the second layer 2 is directly adhesively bonded to the fabric 20. Thus, the crimp sleeve 21 is also mechanically fixed to the fabric 20 by means of the adhesive layer 2. An additional fixation is achieved by means of the rivet stud 22a of the connector element 22 which extends through the fabric 20 and, accordingly, mechanically fixes the connector element 22 and, thus, the entire connector to the fabric 20. It should be noted that components of the connector element may also extend over the seam tape for further mechanical fixation (not shown). For example, if the connector element comprises a rivet-like snap button assembly, the top and bottom parts of the snap button assembly may extend over the seam tape, thus mechanically fixating the seam tape ends between the top and bottom parts of the snap button.

Moreover, all embodiments shown in FIGS. 16 to 19 comprise an optional reinforcement layer which further mechanically stabilizes the connection between the connector and the seam tape on the one hand and the connector and the fabric on the other hand.

Figure 16:
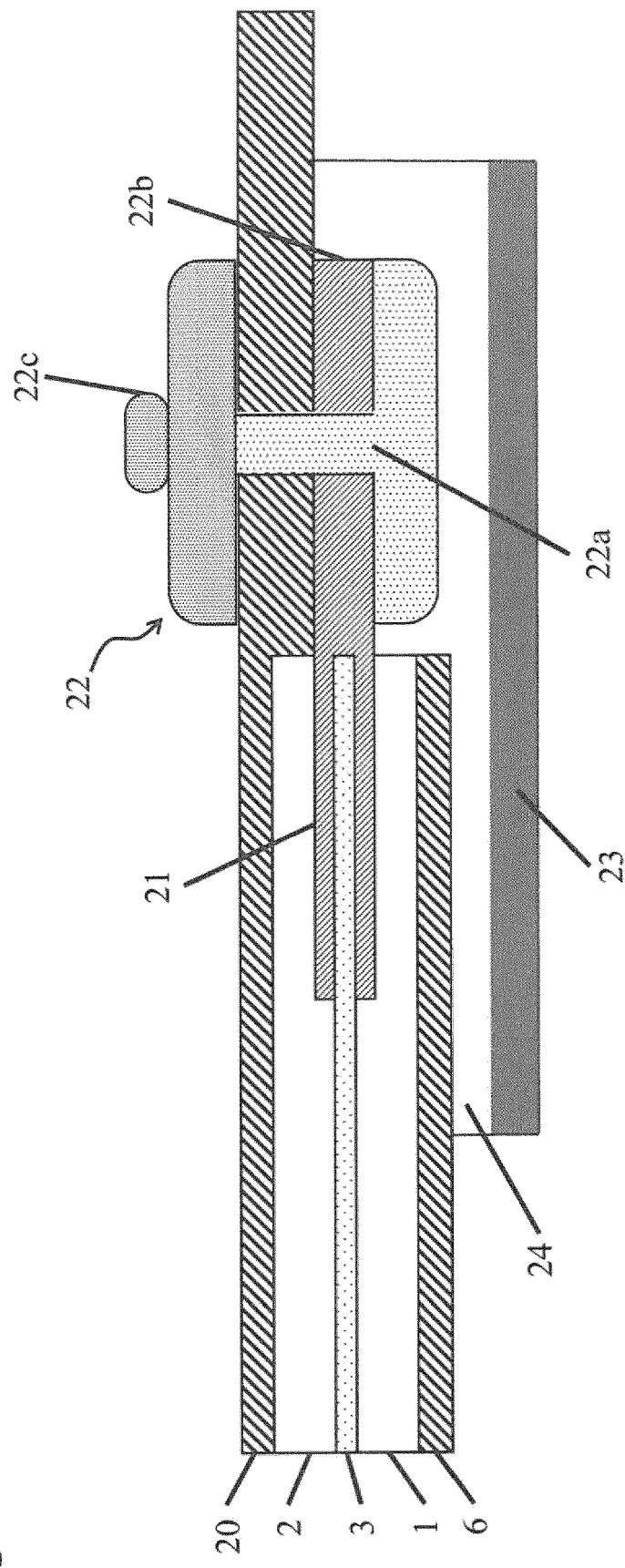
FIG. 16 a longitudinal section through a preferred embodiment of a seam tape according to the present invention being bonded to a fabric.

In the embodiment shown in FIG. 16, a reinforcement layer 23 (which may, for example, be a textile reinforcement layer) is bonded directly to the top layer 6, a part of the connector element 22 and the fabric 20 by means of an additional adhesive layer 24. Accordingly, an end of the seam tape shown in FIG. 16 is enclosed between the fabric 20 on the one hand and the reinforcement layer 23 on the other hand.

Figure 17:
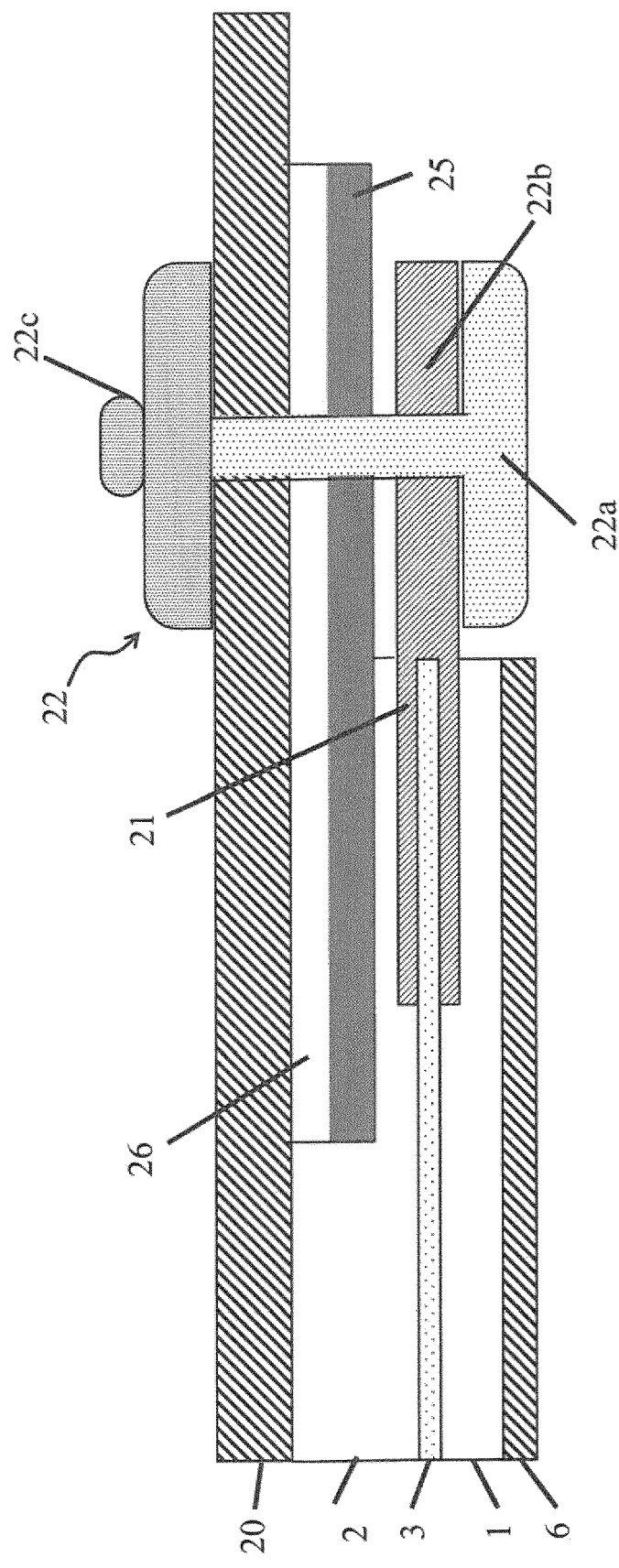
FIG. 17 a longitudinal section through a preferred embodiment of a seam tape according to the present invention being bonded to a fabric.

However, a reinforcement layer 25 may also be provided adjacent to the fabric 20 as shown in FIG. 17. In this case, the reinforcement layer 25 is bonded to the fabric 20 by means of an additional adhesive layer 26. On the opposite side of the reinforcement layer 25, said reinforcement layer 25 is bonded to the crimp sleeve 21 by means of the adhesive layer 2. Due to its positioning between the crimp sleeve 21 and the fabric 20, the reinforcement layer 25 may also be in mechanical contact with the connector element 22, the rivet stud 22a of which extends through the reinforcement layer 25 as shown in FIG. 17.

Figure 18:
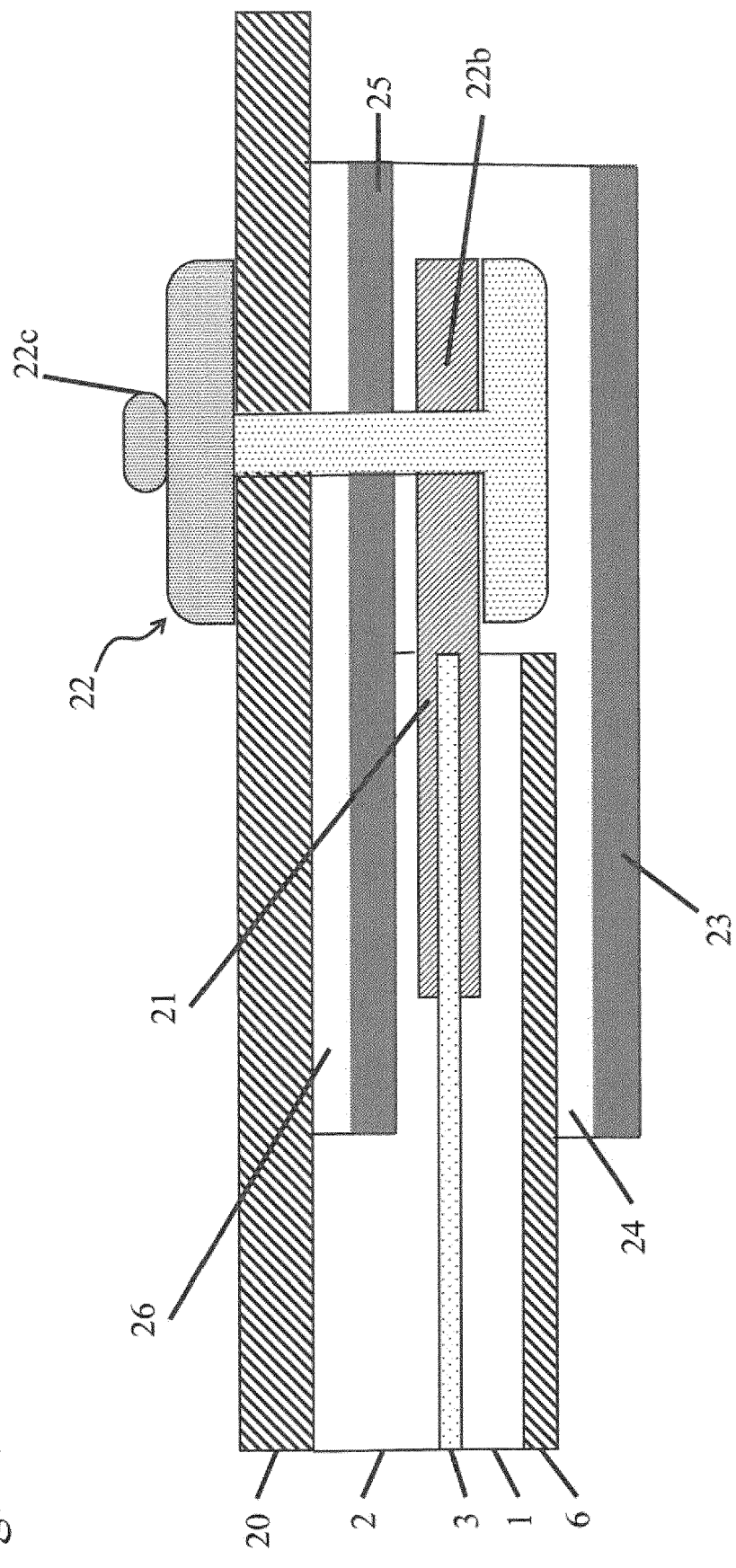
FIG. 18 a longitudinal section through a preferred embodiment of a seam tape according to the present invention being bonded to a fabric.

Of course, the concepts shown in FIG. 16 and FIG. 17 may also be combined as shown in FIG. 18.

Figure 19:
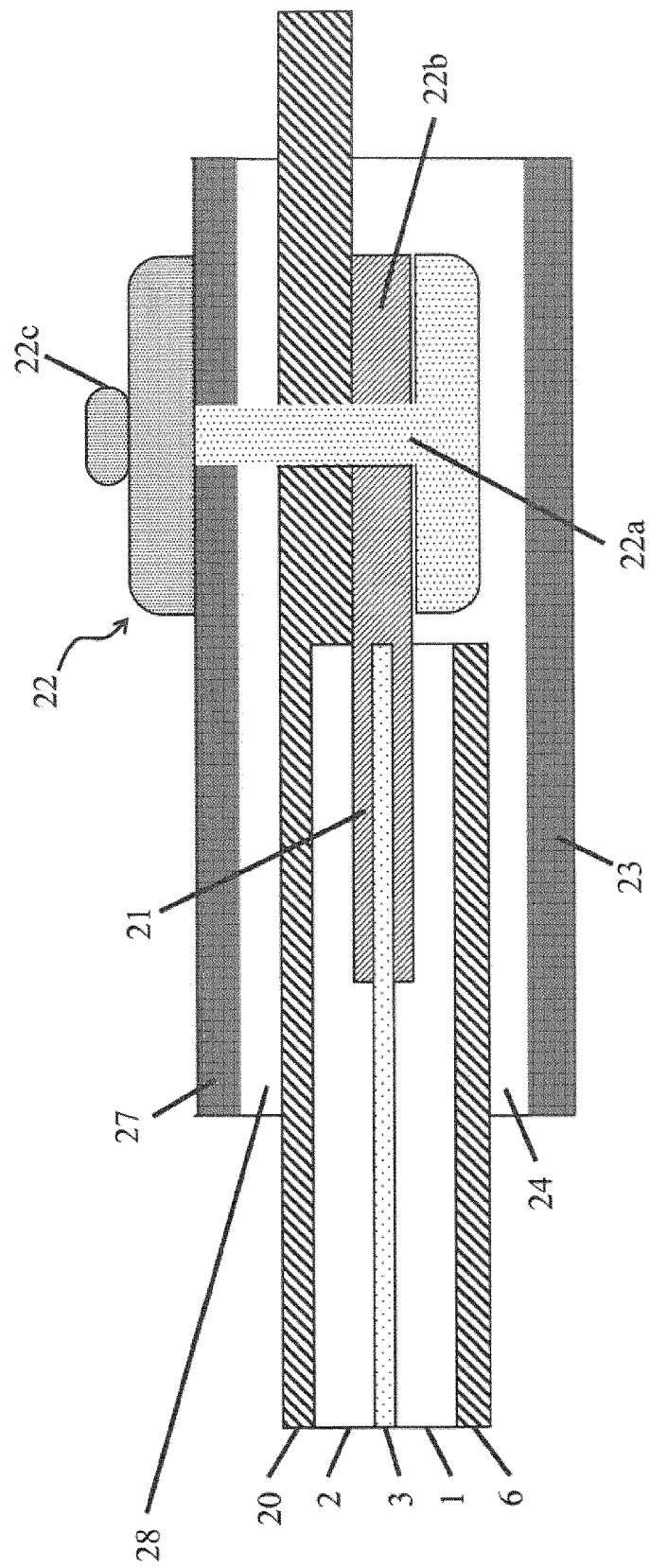
FIG. 19 a longitudinal section through a preferred embodiment of a seam tape according to the present invention being bonded to a fabric.

Finally, a reinforcement layer 27 may also be provided on the opposite side of the fabric 20 as shown in FIG. 19. In this case, the end of the seam tape is enclosed between reinforcement layers 23 and 27 with reinforcement layer 27 being bonded to the fabric 20 by an additional adhesive layer 28. Again, the rivet stud 22a of the connector element 22 extends through the reinforcement layer 27 as shown.

As is evident from the above, the present invention allows for a robust connection to conductors embedded in seam tapes. In particular, the embodiments discussed provide for robustness of the electrical contact to mechanical stresses, robustness of the mechanical contact to mechanical stresses, avoidance of damage to the soft conductor in the transition region between rigid and soft conductors and ease of production and cost of the connector solution. Inter alia, the connector of the present invention disconnects the electrical contact from the mechanical fixation, providing a sufficient strain relief mechanism. In the simplest embodiment, the connector may be based on commercially available crimp-type sockets or ring-tongue terminals. The sleeve of these crimp-type sockets may be inserted directly into the lumen of the seam tape. The crimp is then closed and the tape is ready for lamination. After lamination, rivet buttons may be applied with the shaft of the rivet stud inserted into the ring of the crimp-type socket. Electronic components can then be connected via the buttons. Additional strain relief is obtained due to use of, for example, a more rigid textile as reinforcement layer as discussed above.

The invention claimed is:

1. An elongated elastic seam tape, comprising:
   an elongated elastic first layer comprising an elastic polyurethane,
   an elongated elastic second layer partially bonded to the elongated elastic first layer and comprising an elastic polyurethane;
   an elongated elastic textile layer, wherein the elongated elastic textile layer is bonded to the elongated elastic first layer; and
   an elongated elastic conductor;
   wherein each longitudinal edge of the elongated elastic second layer is bonded to a corresponding longitudinal edge of the elongated elastic first layer so as to form a lumen extending along the entire elongated elastic seam tape between the elongated elastic first and second layers, wherein the lumen extends along an entire length of the elongated elastic seam tape, wherein the lumen opens at an end of the elongated elastic seam tape; and
   wherein the elongated elastic conductor is movably positioned within said lumen, wherein the elongated elastic conductor comprises an elastic core and a conductive wire wrapped around the elastic core.

2. The elongated seam tape of claim 1, wherein the elongated elastic conductor remains electrically conductive at a strain of at least 50%.

3. The elongated seam tape of claim 2, wherein the elongated elastic conductor remains electrically conductive at a strain of at least 75%.

4. The elongated seam tape of claim 2, wherein the elongated elastic conductor remains electrically conductive at a strain of at least 100%.

5. The elongated seam tape of claim 1, wherein the lumen has a first cross-sectional area and wherein the elongated elastic conductor has a second cross-sectional area and wherein the ratio between the first and second cross-sectional areas is at least 1.4.

6. The elongated seam tape of claim 5, wherein the ratio between the first and second cross-sectional areas is at least 2.

7. The elongated seam tape of claim 5, wherein the ratio between the first and second cross-sectional areas is at least 5.

8. The elongated seam tape of claim 1, wherein the melting point of a material of the elongated elastic first layer is higher than that of a material of the elongated elastic second layer.

9. The elongated seam tape of claim 1, wherein the elongated elastic conductor is pre-stretched within said lumen.

10. The elongated seam tape of claim 1, wherein the elongated elastic second layer is configured to be peeled off of the elongated elastic first layer at least at one longitudinal end of the elongated elastic seam tape so as to expose a section of the elongated elastic conductor.

11. The elongated seam tape of claim 10, wherein the elongated elastic second layer is configured to be manually peeled off of the elongated elastic first layer.

12. The elongated seam tape of claim 1, wherein each longitudinal edge of the elongated elastic second layer is bonded to a corresponding longitudinal edge of the elongated elastic first layer and one or more intermediate longitudinal sections of the elongated elastic second layer are bonded to one or more corresponding intermediate longitudinal sections of the elongated elastic first layer so as to form two or more lumina extending along the entire length of the elongated elastic seam tape between the elongated elastic first and second layers, wherein one of said two or more lumina forms the lumen, and wherein a second elongated elastic conductor is movably positioned within another one of said two or more lumina.

13. The elongated seam tape of claim 1, further comprising:
an elongated elastic third layer;
an elongated elastic fourth layer, partially bonded to the elongated elastic third layer; and
an elongated elastic second conductor;
wherein each longitudinal edge of the elongated elastic fourth layer is bonded to a corresponding longitudinal edge of the elongated elastic third layer so as to form a second lumen extending along the entire length of the elongated elastic seam tape between the elongated elastic third and fourth layers;
wherein the elongated elastic second conductor is movably positioned within said second lumen; and
wherein the elongated elastic third layer is different from the elongated elastic second layer or wherein the elongated elastic third layer is integral with the elongated elastic second layer.

14. The elongated seam tape of claim 1, further comprising an electrical connector connected to one end of the elongated elastic conductor.

15. The elongated seam tape of claim 14, wherein the electrical connector comprises a crimp sleeve attached to the end of the elongated elastic conductor and a connector element longitudinally protruding from the lumen of the elongated elastic seam tape.

16. The elongated seam tape of claim 15, wherein the elongated elastic conductor in its unstretched equilibrium state has a first length and wherein the lumen in the unstretched equilibrium state of the elongated elastic seam tape has a second length greater than the first length.

17. The elongated seam tape of claim 15, wherein the connector element comprises a metal ring and a conductive rivet-type snap button connector, wherein the rivet-type snap button connector comprises a rivet stud, and wherein the rivet stud extends through an opening of the metal ring of the connector element.

18. The elongated seam tape of claim 15, wherein the crimp sleeve in the unstretched equilibrium state of the elongated elastic seam tape is completely withdrawn into the lumen of the elongated elastic seam tape.

19. The elongated seam tape of claim 18, wherein the elongated elastic first and second layers comprise an adhesive and wherein the lumen is sealed by the connector element and the adhesive surrounding the connector element.

20. A fabric comprising a reinforcement layer and the elongated elastic seam tape of claim 15 bonded thereto, wherein, in at least one cross section through the fabric, material of the fabric is positioned under the crimp sleeve of the connector element and material of the reinforcement layer is positioned above the crimp sleeve.

21. A fabric comprising the elongated seam tape of claim 14 bonded thereto.

22. The fabric of claim 21, wherein the electrical connector comprises a crimp sleeve attached to an end of the elongated elastic conductor and a connector element longitudinally protruding from the lumen of the elongated elastic seam tape, wherein the crimp sleeve of the electrical connector is adhesively bonded to the elongated elastic first and/or second layer of the elongated elastic seam tape and/or to the fabric.

23. The fabric of claim 21, further comprising a reinforcement layer adhesively bonded to the fabric.

24. The fabric of claim 23, wherein the reinforcement layer is adhesively bonded to a part of the elongated elastic seam tape different from the electrical connector and/or wherein the reinforcement layer is adhesively bonded to the electrical connector of the elongated elastic seam tape.

25. The fabric of claim 23, wherein the reinforcement layer is a textile reinforcement layer.

26. The fabric of claim 21, wherein the elongated elastic second layer of the elongated elastic seam tape is adhesively bonded to the fabric.

27. The elongated seam tape of claim 1, wherein the elastic polyurethane of the elongated elastic first layer is a thermoplastic elastic polyurethane.

28. A method of manufacturing an elongated elastic seam tape, the method comprising the following steps:
providing first and second elongated elastic layers comprising an elastic polyurethane, an elongated elastic textile bonded to the first elongated elastic layer, and an elongated elastic conductor positioned between the first and second elongated elastic layers, wherein the elongated elastic conductor comprises an elastic core and a conductive wire wrapped around the elastic core; and
bonding each longitudinal edge of the second elongated elastic layer to a corresponding longitudinal edge of the first elongated elastic layer such that a lumen extending along an entire length of the elongated elastic seam tape between the first and second elongated elastic layers is formed and such that the elongated elastic conductor extends along said lumen, wherein the lumen opens at an end of the elongated elastic seam tape.

29. The method according to claim 28, wherein the elongated elastic conductor is provided in a pre-stretched configuration and wherein the pre-stretched elongated elastic conductor extends along the entire length of the lumen while the first and second elongated elastic layers are in their unstretched equilibrium state.

* * * * *